US007473428B2

(12) United States Patent
Johnson et al.

(10) Patent No.: US 7,473,428 B2
(45) **Date of Patent: *Jan. 6, 2009**

(54) RECOMBINANT PORCINE ADENOVIRUS VECTOR

(75) Inventors: Michael A. Johnson, Thornbury (AU); Jeffrey Hammond, Jan Juc (AU); Richard J. McCoy, North Balwyn (AU); Michael G. Sheppard, Eltham (AU)

(73) Assignee: VectoGen Pty Ltd., New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 11/387,026

(22) Filed: Mar. 22, 2006

(65) Prior Publication Data

US 2006/0263387 A1 Nov. 23, 2006

Related U.S. Application Data

(63) Continuation of application No. 09/485,512, filed as application No. PCT/AU98/00648 on Aug. 14, 1998, now Pat. No. 7,323,177.

(30) Foreign Application Priority Data

Aug. 14, 1997 (AU) .................................... PO8560

(51) Int. Cl.
*A61K 39/235* (2006.01)
*A61K 39/295* (2006.01)

(52) U.S. Cl. ................. 424/199.1; 424/233.1; 424/93.2

(58) Field of Classification Search ....................... None
See application file for complete search history.

(56) References Cited

U.S. PATENT DOCUMENTS 6,492,343 B1 12/2002 Reddy et al.

FOREIGN PATENT DOCUMENTS

| | | |
|---|---|---|
| AU | 714867 | 2/1995 |
| WO | WO-95/02697 | 1/1995 |
| WO | WO-96/10642 | 4/1996 |
| WO | WO-97/20036 | 6/1997 |
| WO | WO-99/08706 | 2/1999 |
| WO | WO-99/53047 | 10/1999 |

OTHER PUBLICATIONS

Adam et al., "Vaccination of pigs with replication-defective adenovirus vectored vaccines: the example of psuedorabies," Vet. MIcrobiology 42:205-215 (1994).

Beard et al., "Characterization of an 11K Protein Produced by Early Region 3 of Mouse Adenovirus Type 1," Virology, 208:457-466 (1995).

Beard et al., "Transcription Mapping of Mouse Adenovirus Type 1 Early Region 3," Virology, 175:81-90 (1990).

Bett, et al., "An efficient and flexible system for construction of adenovirus vectors with insertions or deletions in early regions 1 and 3," Proc. Natl. Acad. Sci. USA 91:8802-8806 (1994).

Callebant, et al., "Construction of a recombinant adenovirus for the expression of the glycoprotein S antigen of porcine respiratory coronavirus," Coronavirus 469-470 (1994).

Callebaut et al., "Development of a recombinant vector virus for vaccination against viral diarrhea and respiratory disease in pigs," Medelingen van de Faculteit Landbouwwetenschappen Universitei Gent, Gent, BE, 57(4B):2077-2084 (1992).

Cauthen et al., "Novel Expression of Mouse Adenovirus Type 1 Early Region 3 gp11K at Late Times after Infection," Virology 259:119-128 (1999).

Cauthen et al., "Sequence of the mouse adenovirus type-1 DNA encoding the 100-kDA, 33-kDA and DNA-binding proteins," Gene, 168:183-187 (1996).

Chartier, et al., "Efficient generation of recombinant adenovirus vectors by homologous recombination in *Escherichia coli*," J. Virology, Am. Soc. Microbiology, 70(7);4805-4810 (1996).

Derbyshire et al., "Serological and Pathogenicity Studies with Some Unclassified Porcine Adenoviruses," Journal of Comparative Pathology, vol. 85(3):437-443 (1975).

Gorziglia et al., "Expression of the OSU rotavirus outer capsid protein VP4 by an adenovirus recombinant," J. Virology 66(7):4407-4412 (1992).

Graham et al., "Characteristics of a Human Cell Line Transformed by DNA from Human Adenovirus Type 5," Journal of General Virology, vol. 36, pp. 59-74 (1977).

Graham et al., "Methods for construction of adenovirus vectors," Molecular Biotechnology 3(3):207-220 (1995).

Hirahara et al., "Isolation of Porcine Adenovirus from the Respiratory Tract of Pigs in Japan," Japan Journal of Veterinary Science. 52(2):407-409 (1990).

Horwitz, "Adenoviruses," Fields Virology, Third Edition, Chapter 68, pp. 2149-2171 (1996).

Imler et al., "Trans-Complementation of E1-Deleted Adenovirus: A New Vector to Reduce the Possibility of Codissemination of Wild-Type and Recombinant Adenoviruses," Human Gene Therapy, vol. 6, pp. 711-721 (1995).

Kleiboeker et al., "Genomic cloning and restriction site mapping of a porcine adenovirus isolate: demonstration of genomic stability in porcine adenovirus," Arch. Virol 133:357-368 (1993).

Konig et al. "Classical Swine Fever Virus: Independent Induction of Protective Immunity by Two Structural Glycoproteins Journal of Virology," 69(10):6479-6486 (1995).

McCoy et al., "Genomic location and nucleotide sequence of a porcine adenovirus penton base gene," Arch. Virol. 141(7):1367-75 (1996).

(Continued)

*Primary Examiner*—Mary E Mosher
(74) *Attorney, Agent, or Firm*—Nabeela R. McMillian

(57) ABSTRACT

This invention relates to a recombinant vector including a recombinant porcine adenovirus, stably incorporating and capable of expression of at least one heterologous nucleotide sequence. The nucleotide sequence is preferably one which encodes an antigenic determinant of Hog Cholera Virus or Pseudorabies virus. The further invention relates to a method of production of recombinant vectors, to methods of preparation of vaccines based on the vectors, to administration strategies and to methods of protecting pigs from disease.

58 Claims, 15 Drawing Sheets

OTHER PUBLICATIONS

McCoy et al., "Nucleotide and amino acid sequence analysis of the porcine adenovirus 23K protein," DNA Seq 6(4):251-4 (1996).

McCoy et al., "Nucleotide and amino acid sequence analysis of the 100K protein of a serotype 3 porcine adenovirus," DNA Seq. 8(1-2):59-61 (1997).

Mittal et al., "Development of a bovine adenovirus type 3-based expression vector," J. General Virology, Soc. for General Microbiology 76:93-102 (1995).

Reddy et al., "Comparison of the inverted terminal repetition sequences from five porcine adenovirus serotypes," Virology 212(1):237-9 (1995).

Reddy et al., "Nucleotide sequence and transcription map of porcine adenovirus type 3," Virology 251:414-426 (1998).

Reddy et al., "Porcine adenoviruses types 1, 2 and 3 have short and simple early E-3 regions," Virus Research 43:99-109 (1996).

Reddy et al., "Restriction endonuclease analysis and molecular cloning of porcine adenovirus type 3," Intervirology 36:161-168 (1993).

Reddy et al., "Sequence analysis of a putative pVIII, E3 and fibre regions of porcine adenovirus type 3," Virus Research 36:97-106 (1995).

Shenk, "Adenoviridae: The Viruses and Their Replication," Fields Virology, Third Edition, Chapter 67, 2111-2148 (1996).

Torres et al., "Tropism of human adenovirus type-5 based vectors in swine and their ability to protect against transmissible gastroenteritis coronavirus," J. Virology 70(6):3770-3780 (1996).

Torres, et al., "Induction of antibodies protecting against transmissible gastroenteritis coronavirus (TGEV) by recombinant adenovirus expressing TGEV spike protin," Virology 213:503-516 (1995).

Tuboly et al., "Restriction endonuclease analysis and physical mapping of the genome of porcine adenovirus type 5," Virus Research Amsterdam, NL 37(1):49-54 (1995).

Tuboly, et al. "Potential viral vectors for the stimulation of mucosal antibody responses against enteric viral antigens in pigs," Res. in Vet. Sci. British Vet. Ass., London, GB, 54(3)345-350 (1993).

Xu, et al., "Construction of ovine adenovirus recombinants by gene insertion or deletion of related terminal region sequences," Virology 230:62-71 (1997).

Restriction enzyme maps of the PAV3 gnome

Fig 2.

Total sequence of the PAV Major Late Promoter cassette including the added nucleotides 5' (upstream) of the USF.

Nucleotide base count: 76 A 143 C 187 G 96 T Total 502 bp

| | | | | | | |
|---|---|---|---|---|---|---|
| 1 | GGTGCCGCGG | TCGTCGGCGT | AGAGGATGAG | GGCCCAGTCG | GAGATGAAGG | CACGCGCCCA |
| 61 | GGCGAGGACG | AAGCTGGCGA | CCTGCGAGGG | GTAGCGGTCG | TTGGGCACTA | ATGGCGAGGC |
| 121 | CTGCTCGAGC | GTGTGGAGAC | AGAGGTCCTC | GTCGTCCGCG | TCCAGGAAGT | GGATTGGTCG |
| 181 | CCAGTGGTAG | **TCCACGTGAC** | CGGCTTGCGG | GTCGGGGGG**T** | **ATAAAA**GGCG | CGGGCCGGGG |
| 241 | TGCGTGGCCG | TC*AGTTGCTT* | *CGCAGGCCTC* | *GTCACCGGAG* | *TCCGCGTCTC* | *CGGCGTCTCG* |
| 301 | *CGCTGCGGCT* | *GCATCTGTGG* | *TCCCGGAGTC* | *TTCAGGTCCT* | *TGTTGAGGAG* | *GTACTCCTGA* |
| 361 | *TCGCTGTCCC* | *AGTACTTGGC* | *GTGTGGGAAG* | *CCGTCCTGAT* | *CGCGATCCTC* | *CTGCTGTTGC* |
| 421 | *AGCGCTTCGG* | *CAAACACGCG* | *CACCTGCTCT* | *TCGGACCCGG* | *CGAAGCGTTC* | *GACGAAGGCG* |
| 481 | *TCTAGCCAGC* | *AACAGTCGCA* | *AG* | | | |

The Upstream Stimulatory Factor (USF) and TATA motiff are in bold. The complete leader sequence is italised with the cap site and splice sites between the individual leaders indicated by double underlining or single underlining respectively.

Fig 3.

Individual sequences of the Promoter cassette components:

I. The 5' (upstream) sequence included in the long cassette.

```
1     GGTGCCGCGG TCGTCGGCGT AGAGGATGAG GGCCCAGTCG GAGATGAAGG CACGCGCCCA
61    GGCGAGGACG AAGCTGGCGA CCTGCGAGGG GTAGCGGTCG TTGGGCACTA ATGGCGAGGC
121   CTGCTCGAGC GTGTGGAGAC AGAGGTCCTC GTCGTCCGCG TCCAGGAAGT GGATTGGTCG
181   CCAGTGGTAG
```

II. Sequence including the USF, TATA motiff and sequence to the cap site.

```
1     CCACGTGACC GGCTTGCGGG TCGGGGGGTA TAAAAGGCGC GGGCCGGGGT GCGTGGCCGT
61    C
```

III. First leader sequence.

```
1     AGTTGCTTCG CAGGCCTCGT CACCGGAGTC CGCGTCTCCG GCGTCTCGCG CTGCGGCTGC
61    ATCTGTGGTC CCGGAGTCTT CAG
```

IV. Second leader sequence.

```
1     GTCCTTGTTG AGGAGGTACT CCTGATCGCT GTCCCAGTAC TTGGCGTGTG GGAAGCCGTC
61    CTGATCG
```

V. Third leader sequence.

```
1     CGATCCTCCT GCTGTTGCAG CGCTTCGGCA AACACGCGCA CCTGCTCTTC GGACCCGGCG
61    AAGCGTTCGA CGAAGGCGTC TAGCCAGCAA CAGTCGCAAG
```

Fig 4.

Sequence of the right hand end of the PAV genome this area being a proposed site for insertion of expression cassettes.

Nucleotide base count 183 A 255 C 306 G 204 T Total 948 bases

```
  1 CATCATCAAT AATATACCGC ACACTTTTAT TGCCCCTTTT GTGGCGTGGT GATTGGCGGA
 61 GAGGGTTGGG GGCGGCGGGC GGTGATTGGT GGAGAGGGGT GTGACGTAGC GTGGGAACGT
121 GACGTCGCGT GGGAAAATAA CGTGGCGTGG GAACGGTCAA AGTCCGAGGG GCGGGGTCAA
181 AGTCCGCAGT CGCGGGGCGG AGCCGGCTGG CGGGAATTCC CGGGACTTTC TGGGCGGGTA
                                        EcoRI    SmaI
241 ATCGTTAACG CGGAGGCGGG GGAATTCCGA TCGGACGATG TGGTACTGAT TAACCGACCG
       HpaI              EcoRI
301 CAGGCGTGTC CACATCCGCT GTGGGTATAT CACCGGCGCT CGCGGTGTTC GCTCACACTC
361 GTCTCGGCGC TGTCACAGAG AGAGACACTG AGAGCGAGAC GAGGAGAAAC CGAAAGCGGG
421 GCAGGAGGAG TCACCGGGCC ATCTTCCCAT CAGAGCCCTC TCATGGCCCA CGACCGACTG
481 CTGCTGGCCG CGGTGGCTGA CTGTTGCTCG CCGTGCTCTA TCTGTACTTC GCCTACCTCG
541 CGTGGCAGGA TCGGGACACT CTTCACACTC AGGAGGCCGC CTCTCCTCGC TTCTTCATCG
601 GGTCCAACCA CCAGCCCTGG TGCCCGGATT TTGATTGGCA GGAGCAGGAC GAGCACACTC
661 ACTAGACGTT TAGAAAAAAG ACACACATTG GAACTCATAT ATGTCTGCGG GACCGCATCA
721 GCAGCCCGGT CTGCTGTTGG CTGCGGGTGA GAGGCCTCCG GTAATTCATC AGAACCGCAT
                                      StuI
781 TCATCTGCGC CACGTCCCGA CATATGGTGC TGACGTCAGA ACAGCCCAGC GTGATCCTTT
                                     SacIII
841 TAATGTGCTA GTCTACGTGC CCACTGGGTT TGCTGTGTTT GTGCCGACTG AGCGAGATTT
901 TCAGAGGAGG GATCTGGTCC GTTTCCAGAC CTGCTGCTTC CGGCATCA
```

The Inverted Terminal Repeat (ITR) is shown in bold. Enzyme sites of interest are underlined with the enzyme name below. Putative TATA for E4 region is also shown.

Figure 6:
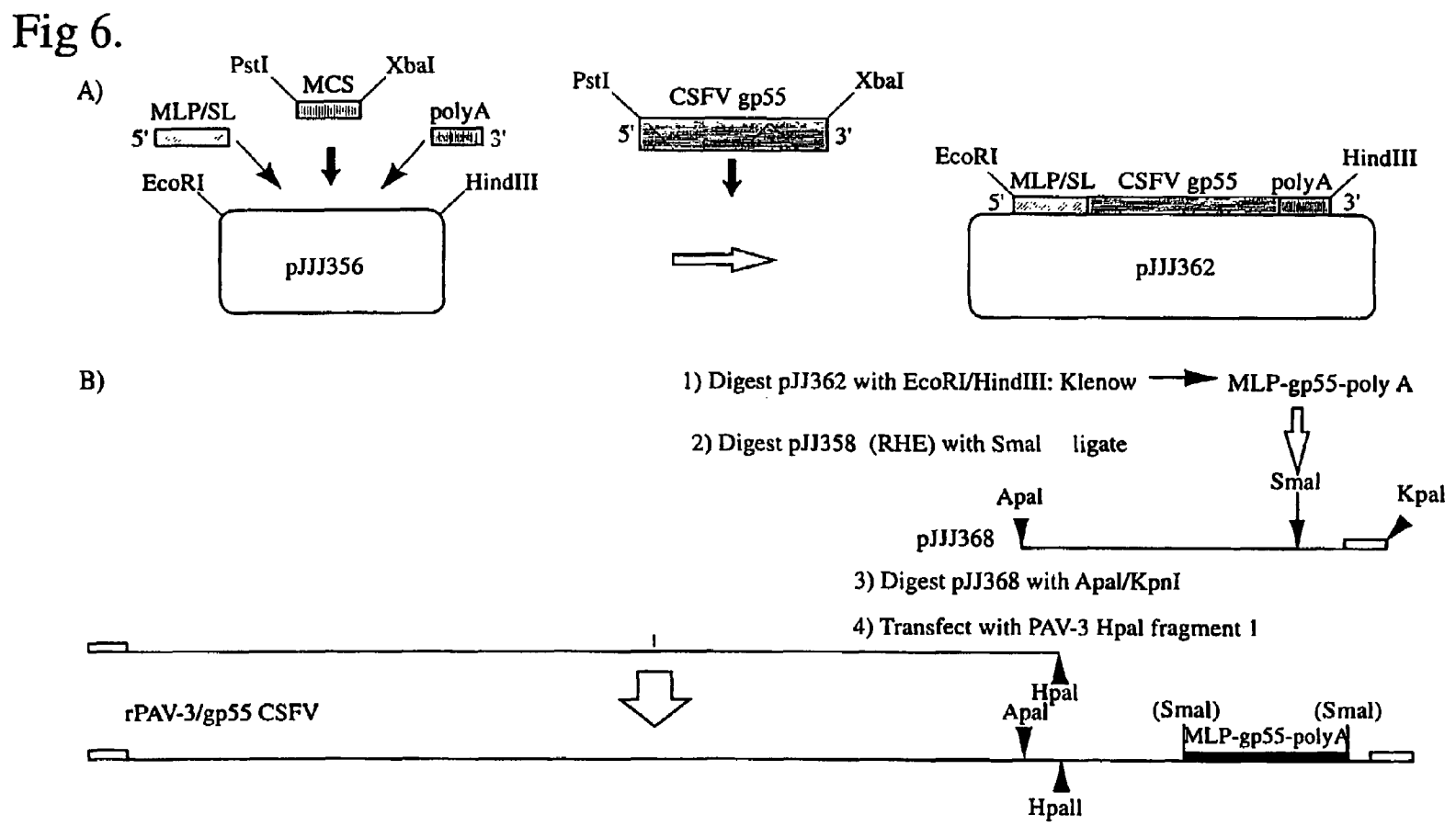

PstI
MCS
XbaI
MLP/SL
5'
polyA
3'
EcoRI
HindIII
pJJJ356

PstI
CSFV gp55
XbaI
5'
3'

EcoRI
MLP/SL
CSFV gp55
polyA
HindIII
5'
3'
pJJJ362

B)

1) Digest pJJ362 with EcoRI/HindIII: Klenow → MLP-gp55-poly A

2) Digest pJJ358 (RHE) with Smal ligate

Apal
Smal
Kpal
pJJJ368

3) Digest pJJ368 with Apal/KpnI

4) Transfect with PAV-3 Hpal fragment 1

Hpal
rPAV-3/gp55 CSFV
Apal
(Smal)
(Smal)
MLP-gp55-polyA
Hpall

Fig 8.

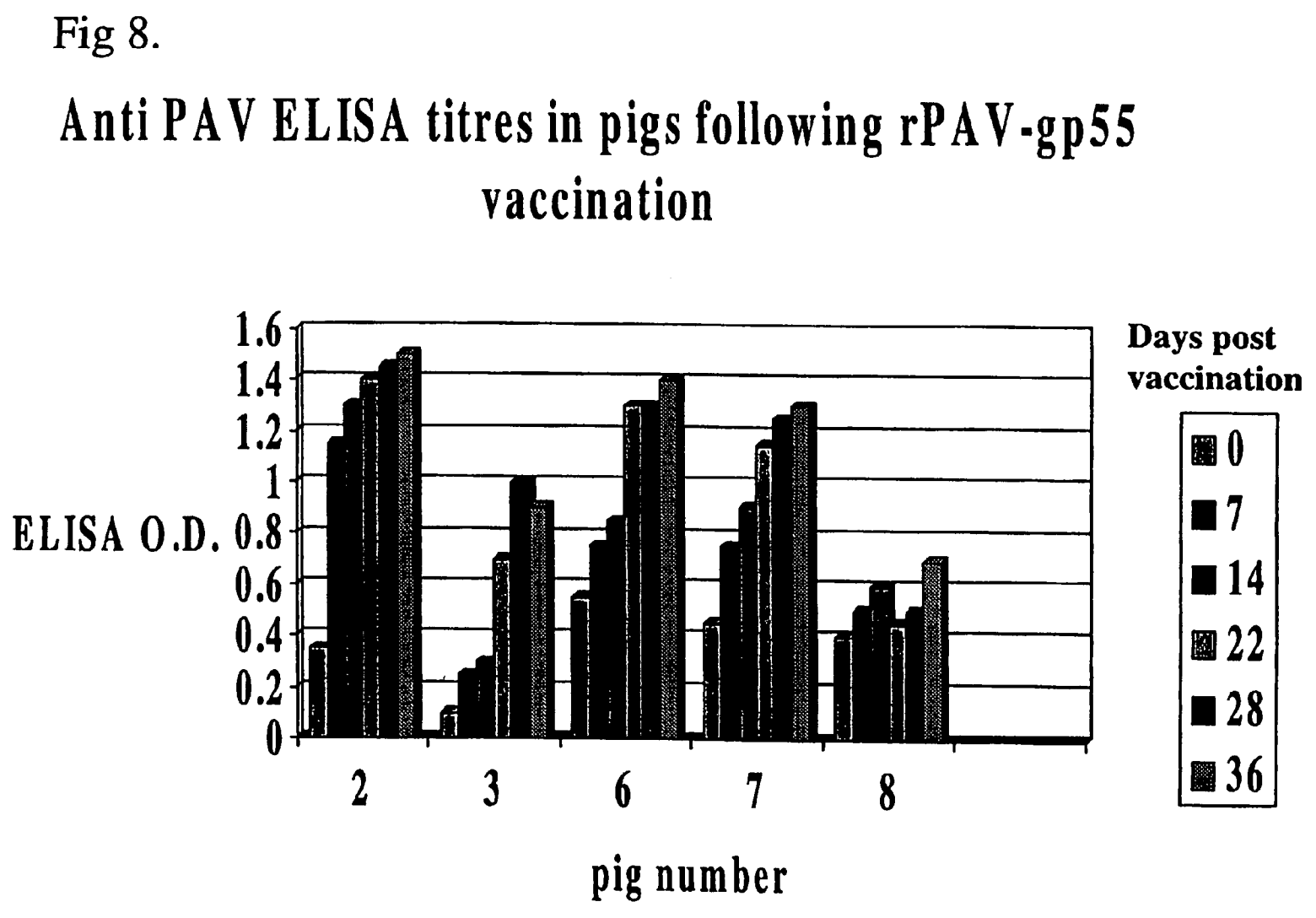

Anti PAV ELISA titres in pigs following rPAV-gp55 vaccination

ELISA O.D.

1.6
1.4
1.2
1
0.8
0.6
0.4
0.2
0

2
3
6
7
8 pig number

Days post vaccination 0
7
14
22
28
36

Fig 9.

CSFV SN Ab titres in pig sera log dilution 10000
1000
100
10
1

2
6
7 pig No.

Days post vaccination
day 0
day 28
day 52 a)
BglII
D
BglII
C
BglII
E
AsuII
LspI
BglII
SgfI
XbaI
A
BglII
F
MunI
BglII
SnaBI
B
HpaI
ITR
PAV3 genome 34,094 bp
b)
RsrII
BsrGI
SnaBI
DrdI
SexAI
HpaI
SmaI
ITR
BglII B 7,236 bp
c)
RsrII
NheI
DrdI
SexAI
HpaI
NotI
SalI
HindIII
ITR
MLP/TPL
gp55
Poly A
MLP/TPL-MCS-Poly A
E3/RHE Insertion vector 9,963 bps

SEQUENCE LISTING

<160> NUMBER OF SEQ ID NOS: 7

<210> SEQ ID NO 1
<211> LENGTH: 502
<212> TYPE: DNA
<213> ORGANISM: Artificial sequence
<220> FEATURE:
<223> OTHER INFORMATION: Recombinant porcine adenovirus major late promoter cassette

<400> SEQUENCE: 1
ggtgccgcgg tcgtcggcgt agaggatgag ggcccagtcg gagatgaagg cacgcgccca 60
ggcgaggacg aagctggcga cctgcgaggg gtagcggtcg ttgggcacta atggcgaggc 120
ctgctcgagc gtgtggagac agaggtcctc gtcgtccgcg tccaggaagt ggattggtcg 180
ccagtggtag tccacgtgac cggcttgcgg gtcggggggt ataaaaggcg cgggccgggg 240
tgcgtggccg tcagttgctt cgcaggcctc gtcaccggag tccgcgtctc cggcgtctcg 300
cgctgcggct gcatctgtgg tcccggagtc ttcaggtcct tgttgaggag gtactcctga 360
tcgctgtccc agtacttggc gtgtgggaag ccgtcctgat cgcgatcctc ctgctgttgc 420

-continued

```
agcgcttcgg caaacacgcg cacctgctct tcggacccgg cgaagcgttc gacgaaggcg    480

tctagccagc aacagtcgca ag                                             502


<210> SEQ ID NO 2
<211> LENGTH: 190
<212> TYPE: DNA
<213> ORGANISM: Artificial sequence
<220> FEATURE:
<223> OTHER INFORMATION: 5'upstream sequence in recombinant adenovirus
      major late promoter cassette

<400> SEQUENCE: 2

ggtgccgcgg tcgtcggcgt agaggatgag ggcccagtcg gagatgaagg cacgcgccca     60

ggcgaggacg aagctggcga cctgcgaggg gtagcggtcg ttgggcacta atggcgaggc    120

ctgctcgagc gtgtggagac agaggtcctc gtcgtccgcg tccaggaagt ggattggtcg    180

ccagtggtag                                                           190


<210> SEQ ID NO 3
<211> LENGTH: 61
<212> TYPE: DNA
<213> ORGANISM: Artificial sequence
<220> FEATURE:
<223> OTHER INFORMATION: Recombinant adenovirus major late promoter
      cassette

<400> SEQUENCE: 3

ccacgtgacc ggcttgcggg tcggggggta taaaaggcgc gggccggggt gcgtggccgt     60

c                                                                     61


<210> SEQ ID NO 4
<211> LENGTH: 83
<212> TYPE: DNA
<213> ORGANISM: Artificial sequence
<220> FEATURE:
<223> OTHER INFORMATION: First leader sequence in recombinant
      adenovirus major late promoter cassette

<400> SEQUENCE: 4

agttgcttcg caggcctcgt caccggagtc cgcgtctccg gcgtctcgcg ctgcggctgc     60

atctgtggtc ccggagtctt cag                                             83


<210> SEQ ID NO 5
<211> LENGTH: 67
<212> TYPE: DNA
<213> ORGANISM: Artificial sequence
<220> FEATURE:
<223> OTHER INFORMATION: Second leader sequence in recombinant
      adenovirus major late promoter cassette

<400> SEQUENCE: 5

gtccttgttg aggaggtact cctgatcgct gtcccagtac ttggcgtgtg ggaagccgtc     60

ctgatcg                                                               67


<210> SEQ ID NO 6
<211> LENGTH: 100
<212> TYPE: DNA
<213> ORGANISM: Artificial sequence
<220> FEATURE:
<223> OTHER INFORMATION: Third leader sequence in recombinant
      adenovirus major late promoter cassette

<400> SEQUENCE: 6
```

-continued

```
cgatcctcct gctgttgcag cgcttcggca aacacgcgca cctgctcttc ggacccggcg     60

aagcgttcga cgaaggcgtc tagccagcaa cagtcgcaag                          100


<210> SEQ ID NO 7
<211> LENGTH: 948
<212> TYPE: DNA
<213> ORGANISM: Porcine

<400> SEQUENCE: 7

catcatcaat aatataccgc acacttttat tgcccctttt gtggcgtggt gattggcgga     60

gagggttggg ggcggcgggc ggtgattggt ggagaggggt gtgacgtagc gtgggaacgt    120

gacgtcgcgt gggaaaataa cgtggcgtgg gaacggtcaa agtccgaggg gcggggtcaa    180

agtccgcagt cgcggggcgg agccggctgg cgggaattcc cgggactttc tgggcgggta    240

atcgttaacg cggaggcggg ggaattccga tcggacgatg tggtactgat taaccgaccg    300

caggcgtgtc cacatccgct gtgggtatat caccggcgct cgcggtgttc gctcacactc    360

gtctcggcgc tgtcacagag agagacactg agagcgagac gaggagaaac cgaaagcggg    420

gcaggaggag tcaccgggcc atcttcccat cagagccctc tcatggccca cgaccgactg    480

ctgctggccg cggtggctga ctgttgctcg ccgtgctcta tctgtacttc gcctacctcg    540

cgtggcagga tcgggacact cttcacactc aggaggccgc ctctcctcgc ttcttcatcg    600

ggtccaacca ccagccctgg tgcccggatt ttgattggca ggagcaggac gagcacactc    660

actagacgtt tagaaaaaag acacacattg gaactcatat atgtctgcgg gaccgcatca    720

gcagcccggt ctgctgttgg ctgcgggtga gaggcctccg gtaattcatc agaaccgcat    780

tcatctgcgc cacgtcccga catatggtgc tgacgtcaga acagcccagc gtgatccttt    840

taatgtgcta gtctacgtgc ccactgggtt tgctgtgttt gtgccgactg agcgagattt    900

tcagaggagg gatctggtcc gtttccagac ctgctgcttc cggcatca                 948
```

RECOMBINANT PORCINE ADENOVIRUS VECTOR

FIELD OF INVENTION

This invention relates to delivery vectors for antigen producing genes (heterologous gene sequences or fragments thereof) used to generate immune responses in commercial pigs susceptible to decimation by disease. Such vectors are especially useful for the preparation of vaccines which can be easily administered on a large scale to protect pigs against disease. This invention also relates to a method of production of suitable delivery vectors, to methods of preparation of vaccines based on the vectors, to administration strategies and to a method protecting pigs from disease.

BACKGROUND

The productivity of the intensive pig industry depends on the control of infectious diseases. Whilst diseases can be controlled in part by good hygiene and quarantine measures, the industry must still rely on vaccination to protect herds. In a commercial situation, the cost per animal is high in terms of feed and current disease control costs and therefore, the costs in disease prevention and control by any newly proposed vaccine must be cheap, effective and easy to deliver.

Conventionally, vaccines constituting live viral particles have been prepared by virus passage and selection of attenuated forms. Alternatively, killed vaccines were prepared from virulent viruses.

The most recent description of the use of viral vectors in the control of disease in pigs was the deletion mutant of pseudorabies virus for the control of Aujesky's disease. The use of a herpesvirus as a vector has the advantage of being able to stimulate a humoral and cell-mediated response, thus providing possible life long protection. Another advantage is the ability to insert other heterologous sequences in this vector, being expressed from a suitable promoter, to produce antigens for exposure to the animals immune system, thus protecting against two diseases. There are disadvantages of this system. Firstly, there is the issue of latency. Herpesviruses have the ability to intergrate into the neurons in ganglia for the life of the animal. It only requires a suitable stress on the animal to cause the reactivation of the virus and consequently full disease. However, it is now known that the deletion of a specific gene, glycoprotein E, will attenuate the virus and prevent reactivation from latency. Therefore, this deletion vector is now widely used as an eradication vector for Aujesky's disease and subsequently will not be available as a suitable vector for the delivery of other antigens.

It is thus the aim of this invention to provide a delivery vehicle for heterologous sequences of genetic material that is particularly suited to administration on a large scale.

In particular, it is the aim of this invention to provide or enhance means for generation and/or optimisation of antibodies or cell-mediated immunity so as to provide protection against infection with common porcine diseases. It is an additional aim to provide a process for preparation of a suitable means for generation and/or optimisation of antibodies or cell-mediated immunity so as to protect pigs against infection with common porcine diseases. It is a further aim to provide a protection strategy.

SUMMARY OF INVENTION

The invention provides, in one embodiment, a recombinant porcine adenovirus capable of expressing DNA of interest said DNA of interest being stably integrated into an appropriate site of said recombinant porcine adenovirus genome.

In another embodiment the invention provides a recombinant vector including a recombinant porcine adenovirus which stably incorporates at least one heterologous nucleotide sequence. Preferably the heterologous nucleotide sequence is capable of expression as an antigenic polypeptide. The antigenic polypeptide encoded by at least one nucleotide sequence is preferably foreign to the host vector.

In a further embodiment of the present invention the heterologous nucleotide sequence is capable of expression as an immuno-potentiator molecule.

It is also to be understood that the heterologous nucleotide sequence may encode for and/or express, an antigenic polypeptide and an immuno-potentiator molecule.

The recombinant vector may comprise a live recombinant porcine adenovirus in which the virion structural proteins are unchanged from those in the native porcine adenovirus from which the recombinant porcine adenovirus is produced.

This invention is partially predicated on the discovery that there are non-essential regions in the porcine adenovirus genome which do not correspond to those characterised previously on other adenoviruses thus making this virus particularly suited to delivery of heterologous sequences.

This invention is also predicated on the discovery that the porcine adenovirus generates a prolonged response in pigs thus making it well suited as a vaccine vehicle. Furthermore, the existence of a number of serotypes specific to respiratory or gastrointestinal tracts, allows the selection of a vaccine vehicle suited to a target organ and the type of immune response required.

The invention is also predicated on the discovery that porcine adenovirus can package genomic DNA greater than the 105% rule for mammalian adenoviruses with intermediate size genomes and that the resultant packaged virions are stable in vitro and in vivo.

Adenoviruses are a large and diverse family, having been isolated from many living species, including man and other mammals as well as a variety of birds. As a result adenoviruses have been separated into at least two genera, the *Mastoadenoviridae* and the *Aviadenoviridae,* and more recently a third genera has been proposed, the *Atadenovirdae,* which includes some bovine and avian adenoviruses (egg drop syndrome) (Benkö and Harrach, Archives of Virology 143, 829-837, 1998).

Porcine adenoviruses are prevalent infectious agents of pigs and to date four distinct serotypes have been recognised (Adair and McFerran, 1976) and evidence for at least one more (Derbyshire et al., 1975). Of the four serotypes found, three (serotypes 1 to 3) were isolated from the gastrointestinal tract while the fourth was recovered from the respiratory system. The porcine adenoviruses are considered to be a low pathogenic widespread agent and although isolations were made in general from diseased animals, it was most likely that the adenovirus was present only as a secondary infection. They have been isolated from pigs with diarrhoea and respiratory infections but it has been considered that at least the gastrointestinal adenovirus infections are usually asymptomatic (Sanford and Hoover, 1983). Porcine adenoviruses are spread by ingestion or inhalation and experimental infection via oral, intranasal and intratracheal inoculations have resulted in uptake of the virus. Experimental pathogenicity studies have shown that the primary sites of infection are the lower small intestine probably the tonsil (Sharpe and Jessett, 1967; Shadduck et al., 1968). With serotype 4 infection, a viraemia appears to develop in experimental infections. However, this may be a less common manifestation with the gastrointestinal serotypes (Shadduck et al., 1968). Faecal excretion is the most common cause for spread of PAV, being present for several weeks post infection. Nasal shedding also occurs under experimental conditions. PAV's role in pneumonia has been suggested to be that of either a predisposing factor or a synergist (Kasza et al., 1969; Schiefer et al., 1974) but experimental pneumonia with serotype 4 did not require a second agent to produce disease (Smith et al., 1973).

Porcine adenoviruses have yet to be examined in much detail and little is known about their role in disease or how common they are. This is due to the fact that they do not produce any significant disease in herds and have failed to draw the interest of industry through loss of production. It is likely that the number of serotypes of porcine adenoviruses is much greater than four and that it probably exists in the majority of pig herds as a normal commensal.

Work done on porcine adenovirus in regards to its morphology and molecular biology, has shown some similarities with other *Mastadenoviruses* examined. Its morphology is that of other adenoviruses examined with an icosahedral capsid containing a core of a double stranded DNA genome. Very little work on the characterisation of the PAV genome has been published (Benkö et al, 1990, Kleiboeker et al., 1993, Reddy et al., 1993, Kleiboeker, 1994). The size of the PAV genome (approx. 34.8 kb) is slightly smaller than that of human adenoviruses (approx. 35.9 kb). One study has shown using hybridisation with DNA probes from the total genome of human adenovirus type 2 that there is reasonable DNA homology between the porcine and human adenoviruses (Benkö et al., 1990). A recent report on the serotype 4 PAV demonstrated that its genomic layout was also similar to that of the human adenoviruses in the area of the L4 and E3 regions (including the 33K and pVIII genes) even though the sequence homology was not as strong as may have been expected (Kleiboeker, 1994).

While choosing appropriate PAV for development as a live vectors to deliver vaccines to pigs, it is important to take into account the natural prevalence of serotypes. Those serotypes not commonly encountered in the field have an obvious advantages over those to which pigs are frequently exposed and to which they may have developed immunity.

A further consideration is the ability of the vector to remain active in the pig beyond the period which maternal antibodies in colostrum protect pigs immediately post-birth.

Other important considerations in choosing potential PAV vectors are pathogenicity and immunogenicity. Preferably live vector viruses should be highly infectious but non-pathogenic (or at least attenuated) such that they do not themselves adversely affect the target species.

The preferred candidates for vaccine vectors are non-pathogenic isolates of serotype 4 (respiratory) and serotype 3 (gastrointestinal). Serotype 3 has been chosen as the serotype of choice due to excellent growth abilities in continuous pig kidney cell lines. The isolation of other serotypes, which seems likely, may well alter this selection. It is notable that the more virulent strains produce a greater antibody response.

Heterologous nucleotide sequences which may be incorporated into non-essential regions of the viral genome and which may encode the antigenic determinants of infectious organisms against which the generation of antibodies or cell-mediated immunity is desirable may be those expressing antigenic determinants of intestinal infections caused by gastrointestinal viruses; for example rotavirus or parvovirus infections, or respiratory viruses, for example parainfluenza virus, or that of Japanese encephalitis.

Heterologous nucleotide sequences which may be incorporated include the antigenic determinants of the agents of:

- Porcine parvovirus
- Mycoplasma hyopneumonia
- Porcine parainfluenza
- Transmissable gastroenteritis (porcine coronavirus)
- Porcine rotavirus
- Hog cholera virus (Classical swine fever)
- Swine dysentery
- African swine fever virus
- Pseudorabies virus (Aujesky's disease virus) in particular, the glycoprotein D of the pseudorabies virus
- Porcine respiratory and reproductive syndrome virus (PRRSV)
- Heterologous nucleotide sequences more preferred for incorporation in the vectors of the invention are those expressing antigenic determinants of porcine parvovirus, porcine rotavirus, porcine coronavirus and classical swine fever virus.

It is also envisaged the heterologous sequences incorporated may be immuno-potentiator molecules such as cytokines or growth promoters, for example porcine interleukin 4 (IL4), gamma interferon (γIFN), granulocyte macrophage colony stimulating factor (GM-CSF), granulocyte colony stimulating factor (G-CSF), FLT-3 ligand and interleukin 3 (IL-3).

The type of immune response stimulated by candidate vectors may affect the selection of heterologous nucleotide sequences for insertion therein. PAV serotypes 1, 2 and 3, which naturally infect via the gut may induce local mucosal immunity and are thus more suitable for infections of the intestines (eg classical swine fever virus). PAV serotype 4, which naturally infects via the respiratory system, may be more suitable for infections of the respiratory tract (eg porcine parainfluenza) may also induce good local immunity.

The DNA of interest which may comprise heterologous genes coding for antigenic determinants or immuno-potentiator molecules may be located in at least one non-essential region of the viral genome.

Non-essential regions of the viral genome which may be suitable for the purposes of replacement with or insertion of heterologous nucleotide sequences may be non-coding regions at the right terminal end of the genome at map units 97 to 99.5. Preferred non-coding regions include the early region (E3) of the PAV genome at map units 81-84.

The heterologous gene sequences may be associated with a promoter and leader sequence in order that the nucleotide sequence may be expressed in situ as efficiently as possible. Preferably the heterologous gene sequence is associated with the porcine adenoviral major late promoter and splice leader sequence. The mammalian adenovirus moor late promoter lies near 16-17 map units on the adenovirus genetic map and contains a classical TATA sequence motif (Johnson, D. C., Ghosh-Chondhury, G., Smiley, J. R., Fallis, L. and Graham, F. L. (1988), Abundant expression of herpes simplex virus glycoprotein gB using an adenovirus vector. Virology 164, 1-14).

The splice leader sequence of the porcine adenovirus senotype under consideration is a tripartite sequence spliced to the 5' end of the mRNA of all late genes.

The heterologous gene sequence may also be associated with a poly adenylation sequence.

Instead of the porcine adenoviral major late promoter, any other suitable eukaryotic promoter may be used. For example, those of SV40 virus, cytomegalovirus (CMV) or human adenovirus may be used.

Processing and poly adenylation signals other than those of porcine adenoviruses may also be considered, for example, that of SV40.

In a further aspect of the invention there is provided a recombinant vaccine for generating and/or optimising antibodies or cell-mediated immunity so as to provide or enhance protection against infection with an infectious organism in pigs, the vaccine including at least one recombinant porcine adenovirus vector stably incorporating at least one heterologous nucleotide sequence formulated with suitable carriers and excipients. Preferably the nucleotide sequence is capable of expression as an antigenic polypeptide or as an immunopotentiator molecule. More preferably, the heterologous nucleotide sequence may encode for and/or express, an antigenic polypeptide and an immuno-potentiator molecule.

The antigenic polypeptide encoded by the at least one nucleotide sequence is preferably foreign to the host vector. At least one nucleotide sequence may be associated with a promoter/leader and a poly A sequence.

The recombinant vaccine may include live recombinant porcine adenovirus vector in which the virion structural proteins are unchanged from that in the native porcine adenovirus from which the recombinant porcine adenovirus is produced.

Preferred vector candidates for use in the recombinant vaccine are PAV isolates of serotype 3 and 4. Use of other serotypes is possible, depending on herd existing immunity and its environment The vaccine may be directed against respiratory and intestinal infections caused by a variety of agents. In order to direct the vaccine against a specific infectious organism, heterologous gene sequences encoding the antigenic determinants of those infectious organisms may be incorporated into non-essential regions of the genome of the porcine adenovirus comprising the vector. If the vaccine is to be used to optimise protection against disease, suitable heterologous nucleotide sequences may be those of immuno-potentiators such as cytokines or growth promoters.

The vaccine may comprise other constituents, such as stabilisers, excipients, other pharmaceutically acceptable compounds or any other antigen or part thereof. The vaccine may be in the form of a lyophilised preparation or as a suspension, all of which are common in the field of vaccine production.

A suitable carrier for such as a vaccine may be isotonic buffered saline.

In a further aspect of the invention, there is provided a method of preparing a vaccine for generation and/or optimisation of antibodies or cell-mediated immunity so as to induce or enhance protection against an infectious organism in a pig, which includes constructing a recombinant porcine adenovirus vector stably incorporating at least one heterologous nucleotide sequence, and placing said recombinant porcine adenovirus vector in a form suitable for administration. Preferably the nucleotide sequence is capable of expression as an antigenic polypeptide although it may also be an immuno-potentiator molecule. More preferably, the nucleotide sequence may encode for and/or express, an antigenic polypeptide and an immuno-potentiatormolecule. The nucleotide sequence is conveniently foreign to the host vector.

Even more preferably, the nucleotide sequence is associated with promoter/leader and poly A sequences.

The form of administration may be that of an enteric coated dosage unit, an inoculum for intra-peritoneal, intramuscular or subcutaneous administration, an aerosol spray, by oral or intranasal application. Administration in the drinking water or in feed pellets is also possible.

In another aspect of the invention, there is provided a method of producing a porcine adenovirus vaccine vector which includes inserting into a porcine adenovirus at least one heterologous nucleotide sequence. Said heterologous nucleotide sequence is preferably capable of expression as an antigenic polypeptide although it may also be an immuno-potentiator molecule. More preferably, the nucleotide sequence may encode for and/or express, an antigenic polypeptide and an immuno-potentiator molecule.

Preferably the antigenic polypeptide encoded by the at least one nucleotide sequence is foreign to the host vector.

More preferably, the heterologous nucleotide sequence is associated with promoter/leader and poly A sequences.

In one method of construction of a suitable vector the non-essential region to be altered to incorporate foreign DNA could be constructed via homologous recombination. By this method the non-essential region is cloned and foreign DNA together with promoter, leader and poly adenylation sequences is inserted preferably by homologous recombination between flanking sequences. By this method also, deletion of portions of the non-essential region is possible to create extra room for larger DNA inserts that are beyond the normal packing constraints of the virus.

By this method a DNA expression cassette containing an appropriate PAV promoter with foreign gene sequence as well as leader sequences and poly adenylaton recognition sequences can be constructed with the unique restriction enzyme sites flanking the cassette enabling easy insertion into the PAV genome.

In another aspect of the invention there is provided strategies for administration of the vaccines of the invention.

In one strategy, a heterologous antigen and immuno-modulatory molecule such as a cytokine may be expressed in the same recombinant and delivered as a single vaccine.

In one strategy according to the invention PAV vector based vaccines may be administered as 'cocktails' comprising 2 or more virus vectors carrying different foreign genes or immuno-potentiators.

In a preferred vaccination strategy of the invention, the 'cocktail' or simultaneous strategy, a vaccine based on both PAV serotype 3 and serotype 4 is used.

In another preferred strategy, a base recombinant serotype 3 porcine adenovirus is constructed and the fiber gene from serotype 4 replacing that of serotype 3 or the fiber from serotype 4 additionally cloned into the vaccine to broaden the targeting of the invention to both gut and respiratory delivery.

In an alternative strategy according to the invention, PAV vector based vaccines may be administered consecutively of each other to either administer booster vaccines or new vaccines at some stage subsequent to initial PAV vaccination, The vaccines used are preferably based on heterologous PAV isolates.

In a preferred version of the "consecutive" strategy, vaccines based on isolates serotypically unrelated are selected so as to achieve maximum protection against infection. In one example of such a strategy a vaccine based on PAV serotype 3 is administered subsequently or prior to vaccination with a vaccine based on PAV serotype 4.

Pigs are conveniently inoculated with vector vaccines according to the invention at any age. Piglets may be vaccinated at 1 day old, breeders may be vaccinated regularly up to point of giving birth and thereafter.

Preferably according to either the consecutive strategy or the cocktail strategy, pigs are vaccinated while still not fully immunocompetent. More conveniently, day-old pigs can be vaccinated for protection against re-infection after a period of 4 weeks subsequent to initial vaccination.

In a further embodiment of the invention there is provided a method for producing an immune response in a pig including administering to the pig an effective amount of a recombinant vaccine according to the invention. An effective amount is an amount sufficient to elicit an immune response, preferably at least $10^4$ $TCID_{50}$ per dose.

The vaccine of the invention may of course be combined with vaccines against other viruses or organisms such as parvovirus or Aujesky's disease at the time of its administration.

In a preferred aspect of this embodiment of the invention, administration is by oral delivery or intra-nasally.

Methods for construction and testing of recombinant vectors and vaccines according to this invention will be well known to those skilled in the art. Standard procedures for endonuclease digestion, ligation and electrophoresis were carried out in accordance with the manufacturer's or suppliers instructions. Standard techniques are not described in detail and will be well understood by persons skilled in the art.

BRIEF DESCRIPTION OF THE DRAWINGS

FIG. 2 illustrates the sequence characterisation and cloning of the major later promoter and splice leader sequences of PAV serotype 3. The sequence is SEQ ID NO:1.

FIG. 3 illustrates the sequences of the major later promoter, upstream enhancer sequence and splice leaders 1, 2 and 3. The 5' (upstream) sequence included in the long cassette=SEQ ID NO:2; the sequence including the USF, TATA motif and sequence to the cap site=SEQ ID NO:3; the first leader sequence=SEQ ID NO:4; the second leader sequence=SEQ ID NO:5; the third leader sequence=SEQ ID NO:6.

FIG. 4 illustrates the terminal 720 bases of the right end of the genome (SEQ ID NO:7).

FIG. 6 illustrates a preferred method of construction of a PAV vector.

FIG. 8 graphically represents anti-PAV antibody levels detected by ELISA in pigs pre and post vaccination with a PAV based vaccine.

FIG. 9 graphically illustrates the development of neutralising antibodies in pigs vaccinated with a PAV based vaccine pre and post challenge with CSFV antigen.

PREFERRED EMBODIMENTS

Aspects of preferred embodiments of the invention based on PAV isolates serotype 3 and serotype 4 will now be described. Whilst these two isolates have been selected because of their sites of infection in the pig, it will be appreciated that other isolates of porcine adenovirus may be more suitable for construction of vaccine vectors provided the criteria for selection described herein before are met.

Figure 1:
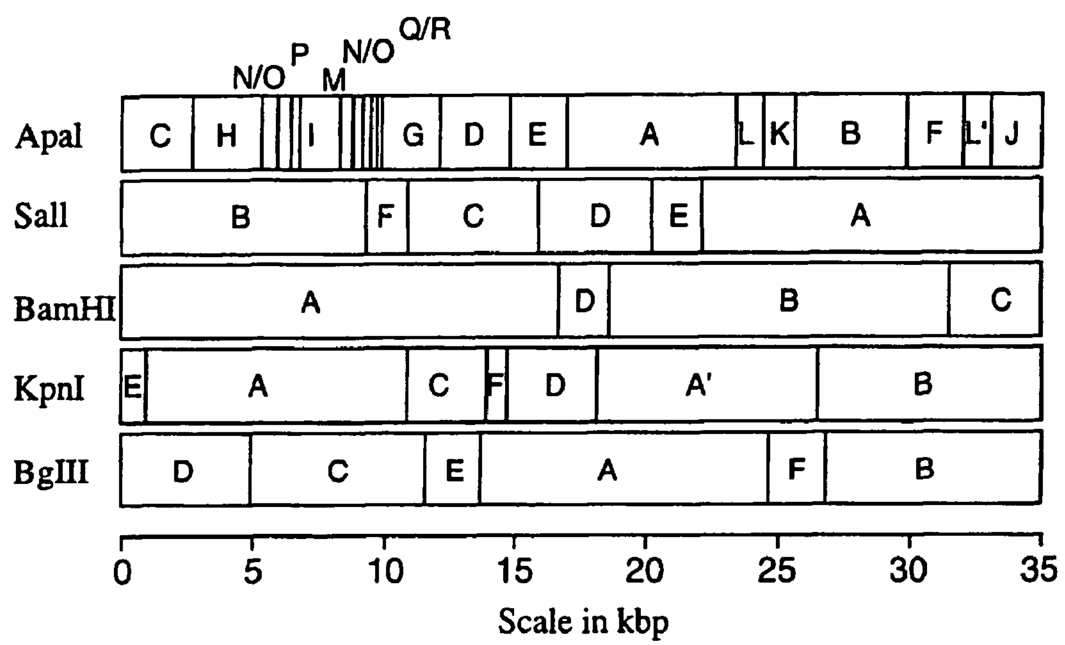
FIG. 1 illustrates the DNA restriction endonuclease map of the entire PAV serotype 3 genome.

In general, PAV are considered of low pathogenicity with little consequence in the field. The pathogenic significance of PAV is reviewed in Derbyshire, 1989. The first report of isolation of PAV was from a 12 day old pig with diarrhoea (Haig et al., 1964). Two years later, PAV type 4 was first reported, isolated from the brain of a pig suffering from encephalitis of unknown cause (Kasza, 1966). Later reports have associated PAV mainly with diarrhoea in the field although this is normally low grade. PAV can also be regularly isolated from healthy animals with no disease signs and it is quite likely that its isolation from diseased animals is more a coincidence of its prevalence than an indicator of pathogenicity. However, an association between serotype 4 and respiratory disease has been reported (Watt, 1978) and this has been supported by experimental infection (Edington et al, 1972). Experimental infections with gastrointestinal serotypes of the virus (eg serotype 3) have been able to produce diarrhoea but the pathological changes produced were not clinically significant The genome of the selected PAV serotype 3 was characterised by conventional methods. The DNA restriction endonuclease maps of the entire genome is illustrated in FIG. 1. The genomes are orientated left to right. By convention adenovirus genomes are normally orientated such that the terminal region from which no late mRNA transcripts are synthesised is located at the left end. The enzymes used to generate the map are indicated at the edge of each map.

Characterisation of Major Late Promoter (MLP) and Splice Leader Sequences (LS) of PAV Serotype 3

Identification and cloning of the PAV MLP

By use of restriction enzyme and genetic maps of the PAV serotype 3 genome, a region was located that contained the MLP and leader sequences (FIG. 1). The fragments identified in this region were cloned into plasmid vectors and sequenced.

The MLP promoter sequence was identified as containing a classical TATA sequence, the only one in the region sequenced, as well as upstream factors and was subsequently confirmed by the location of the leader sequence and the transcriptional start site.

FIGS. 2 and 3 illustrate the sequence characterisation of the major late promoter and splice leader sequences of PAV serotype 3.

In order to determine the structure and sequence of the leader sequence spliced to late mRNA, porcine kidney cells were infected with PAV and the infection was allowed to proceed until late in the infection cycle (usually 20-24 hr p.i.). At this time total RNA was purified from the infected cells using the RNAgents total RNA purification kit (Promega). The isolated RNA was precipitated with isopropanol and stored at −70° C. in 200 μl aliquots until required. Poly A (mRNA) was isolated from total RNA by the use of the Poly AT tract System (Promega, USA). The isolated mRNA was used in cDNA production.

For cDNA production, oligonucleotides were produced to the complimentary strand of the hexon gene and the penton base gene, both being MLP transcripts. A further ollgonucleotide was produced which covered the proposed cap site of the major late transcript, 24 bases downstream of the TATA box. This oligonucleotide was used in conjunction with that used in cDNA production in Taq polymerase chain reaction. The resulting DNA produced from positive clones was digested with appropriate restriction enzymes to determine the size of the inserted fragment. DNA sequencing of these inserted fragments was performed using a modification of the chain termination technique (Sanger, F., Nicklen, S and Gulson, A. R., 1977, DNA sequencing with chain terminating inhibitors. PNAS USA 74: 5463-5467) so as to allow Taq DNA polymerase extension (Promega, USA).

To confirm the leader sequence cap site, fresh cDNA was prepared and this time a tail of dGTP residues added to it. Briefly, cDNA was incubated with 1 mM dGTP and approximately 15 units of terminal deoxynucleotidyl transferase (Promega) in 2 mM CaCl2 buffer at 37° C. for 60 minutes. The reaction was stopped by heating to 70° C. for 10 minutes. The DNA was then ethanol precipitated and resuspended in a volume suitable for use in polymerase chain reaction (PCR). PCR was performed as previously described using a poly (dC) oligonucleotide with a XbaI site at the 5' end. Resulting fragments were blunt ended with T4 DNA polymerase at 37° C. for 30 minutes in the presence of excess nucleotides and cloned into the SmaI site of the pUC18 vector. DNA preparation and sequencing were performed, as described previously, on clones shown to be positive by hybridisation.

FIG. 3 illustrates the separate sequences of the major late promoter, upstream enhancer sequence and splice leaders 1, 2 and 3 as determined from cDNA studies. FIG. 2 illustrates the DNA sequence of the complete promoter cassette with the components joined together.

Characterisation of Non-essential Regions of Viral Genome

The right end was identified by cloning and complete sequencing of the PAV serotype 3 ApaI fragment J of approximately 1.8 Kbp. The inverted terminal repeat (ITR) has been determined by comparison of the RHE sequence with that of the left hand end. The ITR is 144 bases long and represents the starting point into which potential insertions can be made. FIG. 4 shows the sequence of the terminal 720 bases. Restriction endonuclease sites of interest for insertion of foreign DNA are indicated in the terminal sequence. A putative TATA site for the E4 promoter is identified, this being the left most end for the possible site of insertion. Initial insertions will be made into the SmaI or EcoRI sites.

Figure 5:
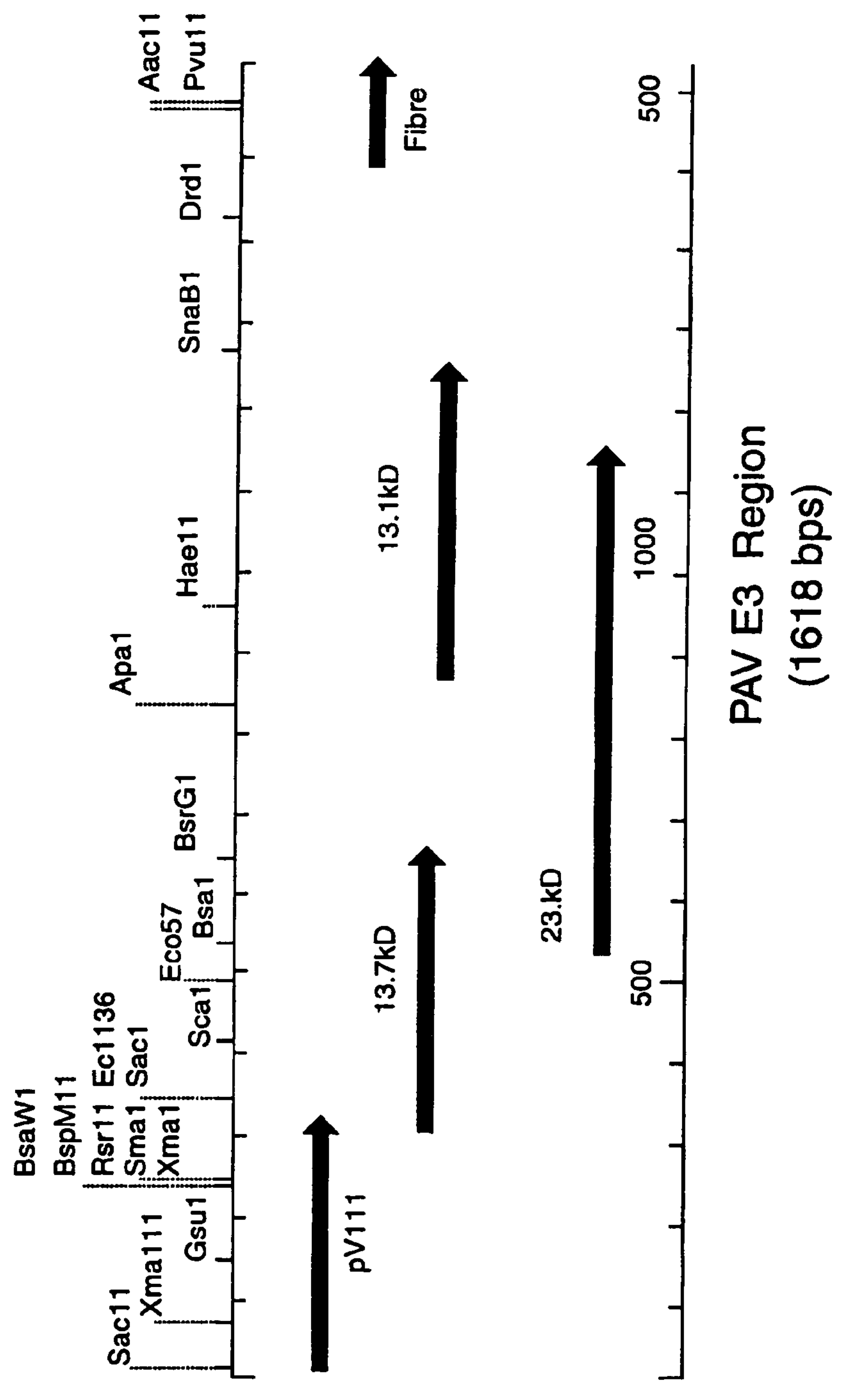
FIG. 5 illustrates the promoter region of E3 and the overlapping L4 area.

The E3 region of the genome, this also being a non-essential area, has been located and cloned. The promoter region of E3 has been identified and the overlapping L4 area sequenced (FIG. 5). The region of the E3 after the polyadenylation signal of the L4 is also a possible site for insertion and can also be used for deletion to create more room for larger cassette insertions.

Construction of PAV Vector

FIG. 6 illustrates a preferred method of construction of a PAV vector. The right hand end ApaI fragment J of PAV serotype 3 is cloned and a unique SmaI restriction endonuclease site 230 bp from the inverted repeats was used as an insertion site.

The major late promoter expression cassette containing the E2 (gp55) gene of classical swine fever virus (hog cholera virus) was cloned into the SmaI site of the RHE fragment.

A preferred method of homologous recombination was cutting genomic PAV 3 DNA with HpaI, a unique site in the genome, and transfecting this DNA with ApaI cut expression cassette plasmid containing gp55.

The DNA mix was transfected into preferably primary pig kidney cells by standard calcium chloride precipitation techniques.

The preferred method of transfection generates recombinant virus through homologous recombination between genomic PAV 3 and plasmid (FIG. 6).

DETAILED DESCRIPTION OF THE INVENTION

Construction of PAV Vector

The following examples show the construction of representative recombinant porcine adenoviruses of this invention. The recombinant viruses were propagated and titred on primary porcine kidney cells.

1 Construction of PAV-gp55

An expression cassette consisting of the porcine adenovirus major late promoter, the classical swine fever virus (CSFV) gene (gp55) and SV 40 polyA was inserted into the SmaI site of the right hand end (MU 97-99.5) of porcine adenovirus serotype 3 and used to generate in porcine primary kidney cells a recombinant PAV 3. The size of the expression cassette was 238 kilobase pairs. No deletion of the genomic PAV 3 was made. Mammalian adenoviruses with intermediate genomes (~36 kb) have been shown to accommodate up to 105% of the wild-type genomic length, and genomes larger than this size are either unpackageable or extremely unstable, frequently undergoing DNA rearrangements (Betts, Prevec and Graham, Journal of Virology 67, 5911-5921 (1993), Packaging capacity and stability of human adenovirus type 5 vectors: Parks and Graham, Journal of Virology, 71, 3293-3298, (1997), A helper dependent system for adenovirus vector production helps define a lower limit for efficient DNA packaging). In this invention, PAV genomic length was 34.8 kb, into which was inserted without any other deletion an expression cassette of 2.38 kb. The resulting genomic DNA length of the recombinant porcine adenovirus of this invention was 106.8%, and therefore exceeded the putative maximum limit for construction of a stable recombinant The recombinant virus was plaque purified three times and passaged stably in primary pig kidney cells. The recombinant was shown to contain gp55 by Southern blot hybridisation. Expression of gp55 was demonstrated by infecting primary PK cell line grown on glass cover slips with the recombinant porcine adenovirus. After 24 hours, immunoflouresencent staining (IF) showed infected cells expressing gp55.

2 Construction of recombinant PAV-G-CSF

An expression cassette comprising of the porcine adenovirus moor late promoter, the gene encoding porcine granulocyte-colony stimulating factor (G-CSF) and SV40 polyA was inserted into the SmaI site of the right hand end (MU 97-99.5) of porcine adenovirus serotype 3 and used to generate in porcine primary kidney cells a recombinant PAV 3. The size of the expression cassette was 1.28 kilobase pairs. No deletion of the genomic PAV 3 was made. The recombinant virus was plaque purified two times and passaged stably in primary pig kidney cells. The recombinant was shown to contain G-CSF by Southern blot hybridisation and polymerase chain reaction (PCR). Expression of G-CSF was demonstrated by infecting primary kidney cells with the recombinant PAV-G-CSF. Tissue culture supernatants from the infected primary kidney cells were then electrophoresed in SDS-PAGE gels and transferred to filters. Infected cells expressing G-CSF were detected in a Western blot using a rabbit polyclonal antiserum against porcine G-CSF expressed by purified recombinant *E coli*.

3 Construction of recombinant PAV-gp55T/GM-CSF

An expression cassette consisting of the porcine adenovirus moor late promoter, a truncated form of the classical swine fever virus gene gp55 fused in frame to the gene encoding either the full length or the mature form of porcine granulocyte/macrophage-colony stimulating factor (GM-CSF) and SV40 polyA was inserted into the SmaI site of the right hand end (MU 97-99.5) of porcine adenovirus serotype 3 and used to generate in porcine primary kidney cells a recombinant PAV 3. The size of the expression cassette was 2.1 kilobase pairs. No deletion of the genomic PAV 3 was made. The recombinant virus was plaque purified two times and shown to contain gp55 and GM-CSF by PCR.

4 Construction of Recombinant PAV-gp55/E3

Figure 15:
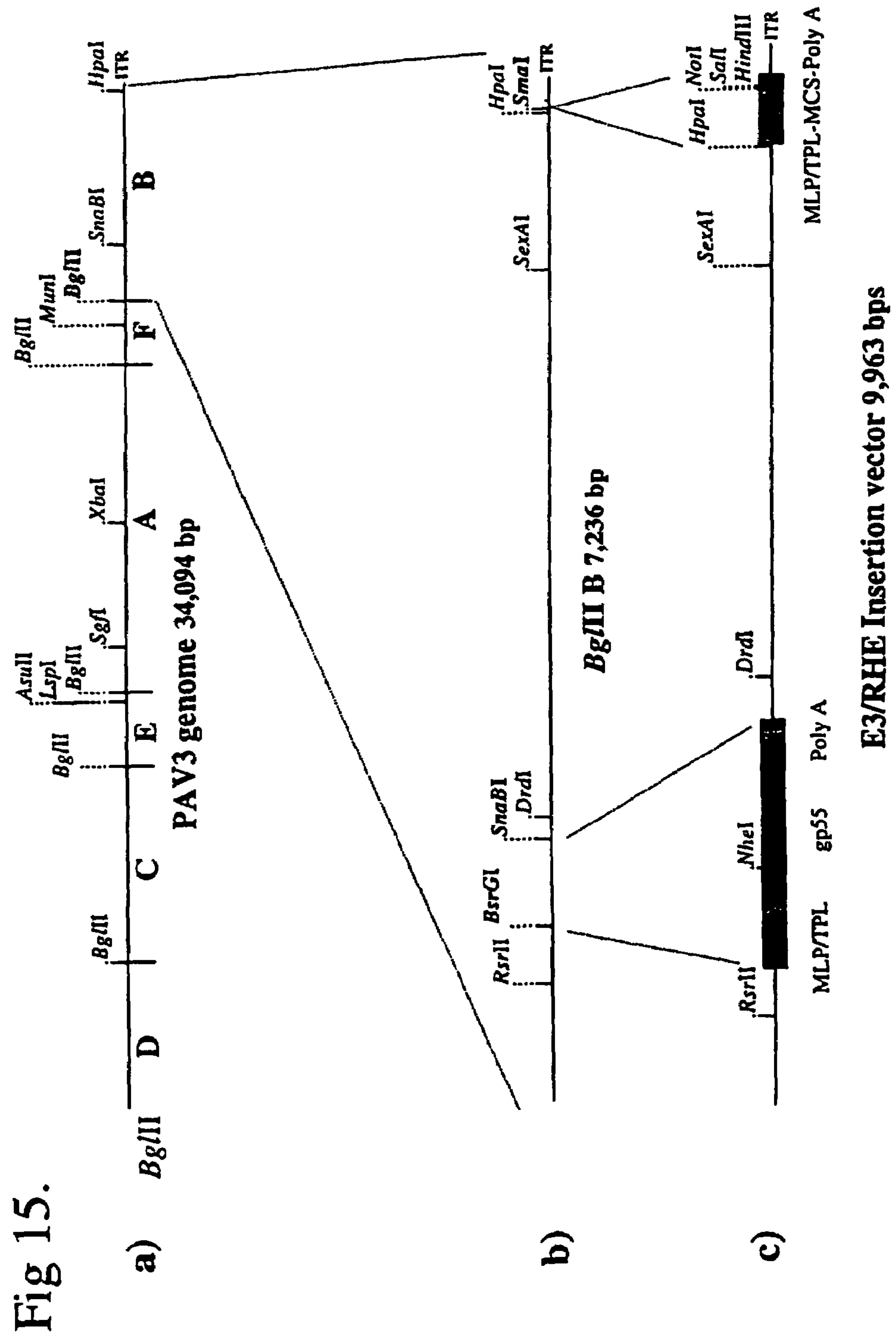
FIGS. 15*a, b* and *c* graphically illustrate a method of construction of a PAV E3 vector.

The insertion vector pJJ408 containing the right hand end ApaI fragment J of the PAV serotype 3 genome (approximately 1.8 kbp), was enlarged to contain the complete BglII B fragment comprising 7.2 kbp of the PAV3 right hand end (FIGS. 15*a* and *b*). This fragment contains both the right hand end insertion site described previously and the E3 region. The right hand end insertion site was engineered to contain the PAV3 MLP/TPL sequences followed by a multiple cloning site and the SV40 poly A sequence.

An E3 insertion site was constructed by excising a 622 bp SnaBI/BsrGI fragment within the E3 region of the PAV serotype 3. The MLP/TPL-gp55-Poly A expression cassette was inserted into the SnaBI/BsrGI site (FIGS. 15*b* and *c*). This plasmid was used in transfections to produce a recombinant PAV3 containing the MLP/TPL-gp55-poly A cassette inserted in the partially deleted E3 region (FIG. 15*c*).

Wild type PAV3 DNA was digested with SnaBI restriction enzyme yielding two fragments of 28.712 kbp and 5.382 kbp. The large left hand fragment which includes the overlap region of the right hand end and the left hand end of the PAV3 genome was gel purified. This fragment was transfected into primary PK cells along with KpnI restricted E3/rhe insertion vector DNA in 3 cm petri dishes to allow homologous recombination to occur between the PAV3 and insertion vector DNA. Using this method, only recombinant virus are recovered.

Cells were maintained for 5 days at 37° C. and then frozen and thawed twice. Lysate was passaged into fresh primary PK cells and observed for the development of plaques. The recombinant virus was plaqued purified and shown to contain gp55 by PCR.

Vaccination Strategy

1. Vaccination with PAV-gp55

In this experiment 5-6 week old piglets were used to represent immunocompetent pigs. A group of the piglets (#2, 6 and 7) were vaccinated with recombinant PAV-gp55 administered subcutaneously at a dose of $1\times10^7$ pfu per piglet A control group of piglets (#3, 8, 11, 12, 13 and 14) were unvaccinated. No clinical signs were observed (no rise in temperature) in the vaccinated group of piglets (Table 1).

| Temperatures post Vaccination with rPAV:: gp55 CSFV (° C.) | | | | | | | | |
|---|---|---|---|---|---|---|---|---|
| Pig No. | Day 0 | 1 | 2 | 3 | 6 | 9 | 10 | 13 |
| 2 | 39.7 | 39.2 | 39.4 | 39.8 | 39.6 | 39.8 | 39.6 | 39.2 |
| 3 (control) | 39.5 | 39.2 | 39.4 | 39.0 | 38.8 | 39.3 | 39.0 | 39.7 |
| 6 | 39.7 | 39.1 | 39.1 | 39.0 | 39.1 | 39.8 | 39.1 | 39.8 |
| 7 | 39.4 | 39.8 | 39.8 | 39.4 | 39.9 | 38.9 | 39.6 | 39.7 |
| 8 (control) | 39.6 | 39.5 | 39.4 | 39.0 | 40.5 | 39.4 | 39.1 | 39.7 |

Five weeks after vaccination with the recombinant PAV-gp55 both groups of pigs were challenged with a lethal dose ($1\times10^{3.5}$ $TCID_{50}$) of virulent Hog Cholera virus (Classical swine fever virus) applied subcutaneously.

Figure 7:
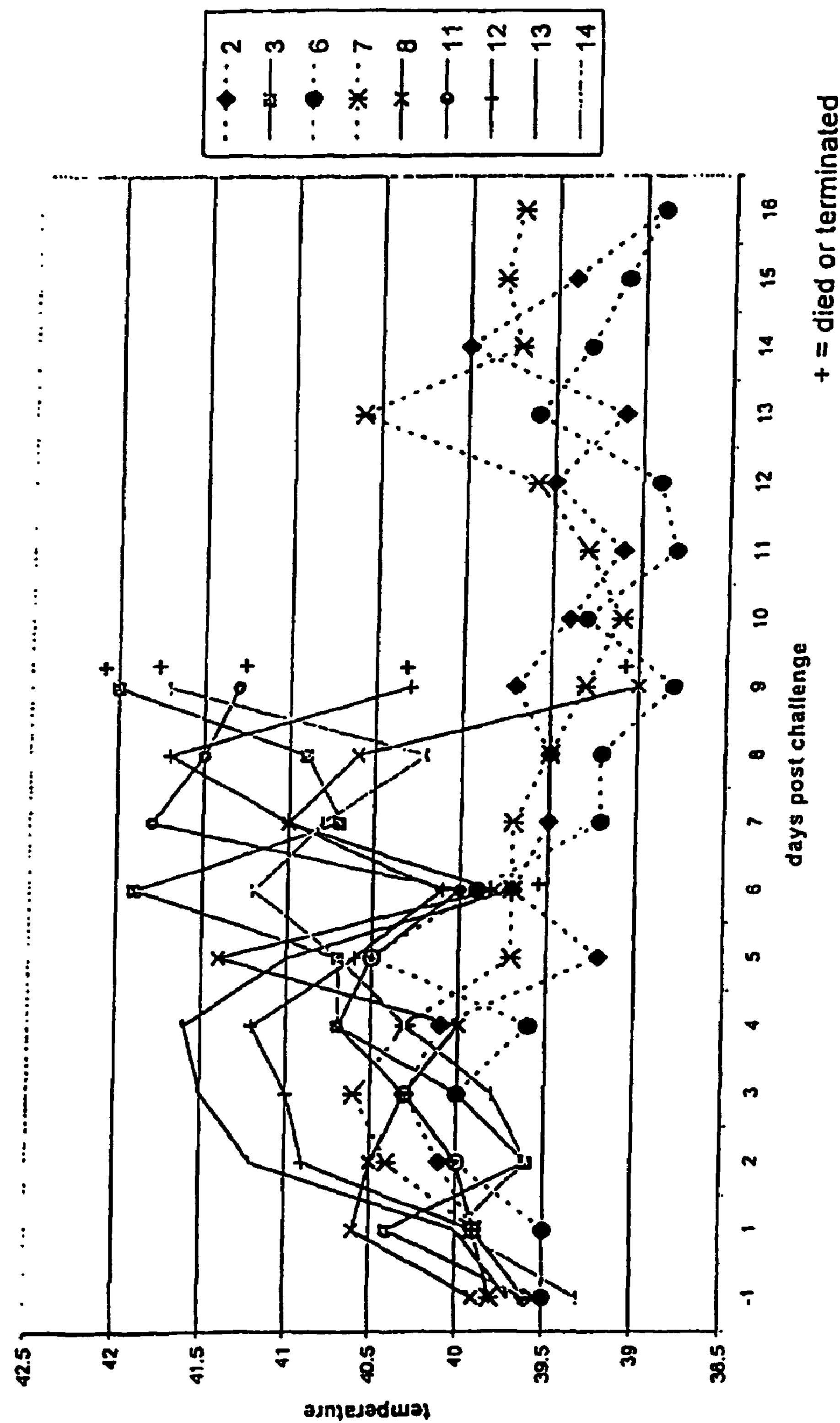
FIG. 7 represents temperature data of pigs vaccinated with a PAV based vaccine following challenge with CSFV antigen.

The temperatures of the pigs were monitored and the results tabulated in Table 2 and graphically represented in FIG. 7.

TABLE 2

| Temperatures post challenge with CSFV (° C.) | | | | | | | | | | | | | | | | | |
|---|---|---|---|---|---|---|---|---|---|---|---|---|---|---|---|---|---|
| | Day | | | | | | | | | | | | | | | | |
| Pig No. | −1 | 1 | 2 | 3 | 4 | 5 | 6 | 7 | 8 | 9 | 10 | 11 | 12 | 13 | 14 | 15 | 16 |
| 2 | 39.6 | 39.9 | 40.1 | 40.3 | 40.1 | 39.2 | 39.7 | 39.5 | 39.5 | 39.7 | 39.4 | 39.1 | 39.5 | 39.1 | 40.0 | 39.4 | 38.9 |
| 3 | 39.6 | 40.4 | 39.6 | 40.0 | 40.7 | 40.7 | 41.9 | 40.7 | 40.9 | 42.0+ | | | | | | | |
| 6 | 39.5 | 39.5 | 40.0 | 40.0 | 39.6 | 40.5 | 39.9 | 39.2 | 39.2 | 38.8 | 39.3 | 38.8 | 38.9 | 39.6 | 39.3 | 39.1 | 38.9 |
| 7 | 39.8 | 39.9 | 40.4 | 40.6 | 40.3 | 39.7 | 39.7 | 39.7 | 39.5 | 39.3 | 39.1 | 39.3 | 39.6 | 40.6 | 39.7 | 39.8 | 39.7 |
| 8 | 39.9 | 40.6 | 40.5 | 40.3 | 40.0 | 41.4 | 39.8 | 41.0 | 40.6 | 39.0+ | | | | | | | |
| 11 | 39.6 | 39.9 | 40.0 | 40.3 | 40.7 | 40.5 | 40.0 | 41.8 | 41.5 | 41.3+ | | | | | | | |
| 12 | 39.8 | 39.9 | 40.9 | 41.0 | 41.2 | 40.6 | 40.1 | 41.0 | 41.7 | 40.3+ | | | | | | | |
| 13 | 39.7 | 40.0 | 41.2 | 41.5 | 41.6 | 41.0 | 39.7+ | | | | | | | | | | |
| 14 | 39.3 | 40.0 | 39.6 | 39.8 | 40.3 | 40.7 | 41.2 | 40.8 | 40.2 | 41.7+ | | | | | | | |

The results show that by day 5 the control group had elevated temperatures (greater than 40.5° C.) and showed clinical signs of disease. The vaccinated group showed no clinical signs of disease. Pigs from the control group were dead or euthanased by day 9. The vaccinated group were euthanased at day 16. At post mortem all control pigs showed severe clinical disease, the vaccinated pigs showed no clinical signs of disease.

The results indicate that the pigs vaccinated subcutaneously with the recombinant PAV-gp55 survived challenge with classical swine fever virus at a lethal dose.

Sera were collected from both groups of pigs and tested for the presence of antibodies to PAV by ELISA. These tests showed the presence of pre-existing antibodies to PAV before vaccination. The level of these antibodies increased following vaccination with the recombinant PAV-gp55 to peak between days 28 and 36 post vaccination. These results are tabulated in FIG. 8.

Figure 9:
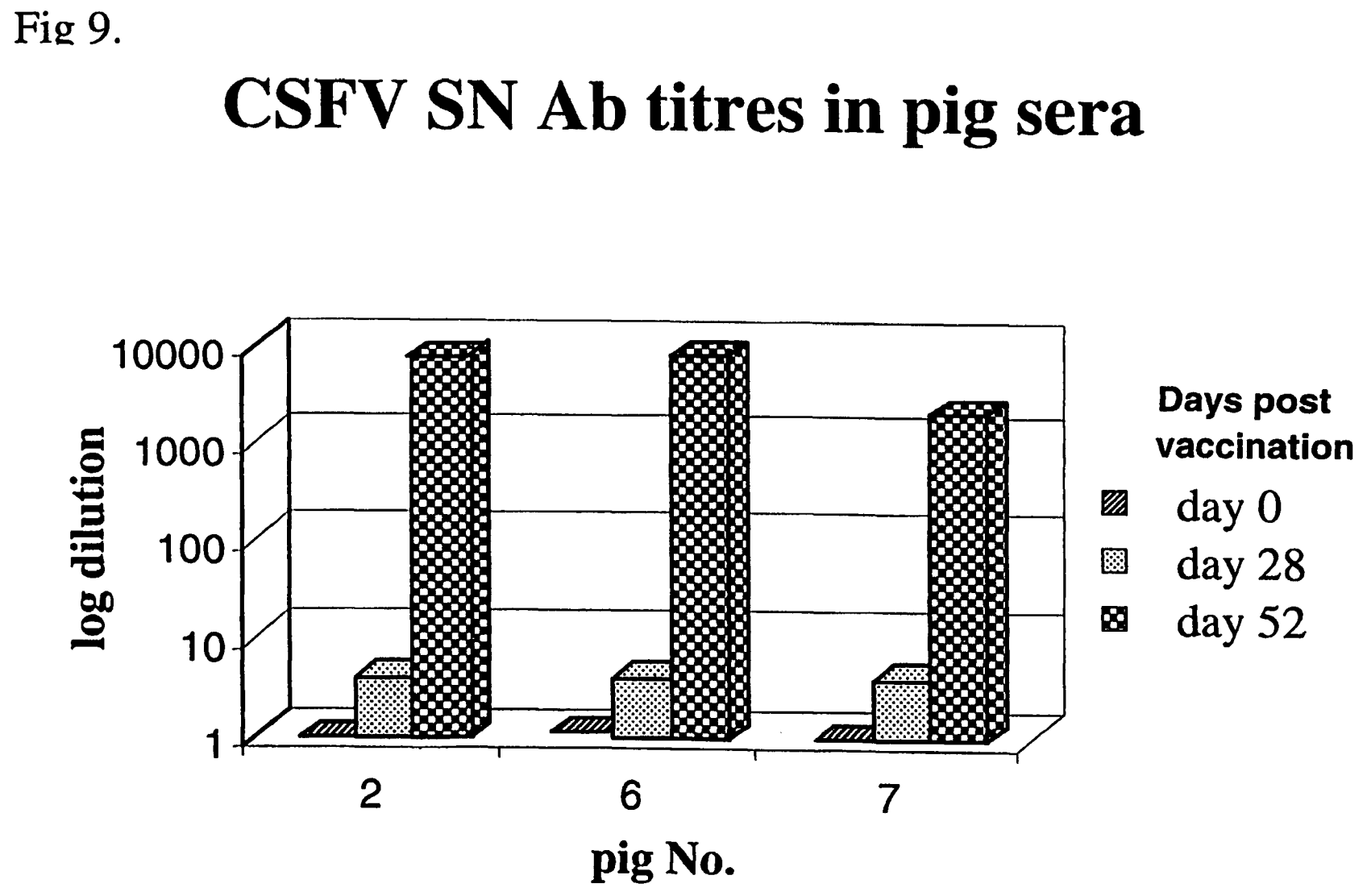

Sera were collected from the vaccinated group of pigs pre and post challenge with CSFV and tested in the presence of neutralising antibodies to CSFV. Sera were tested at days 0 and 28 after vaccination with recombinant PAV-gp55 (pre challenge) and then again at day 16 post challenge (day 52 after vaccination). The results in FIG. 9 show no neutralising antibodies detected at day 0, low levels of neutralising antibodies at day 28 and high levels at day 52.

These results show that the recombinant PAV-gp55 can protect pigs from lethal challenge with classical swine fever virus in the presence of pre-existing antibodies to PAV.

2. Vaccination with PAV-G-CSF

Figure 10:
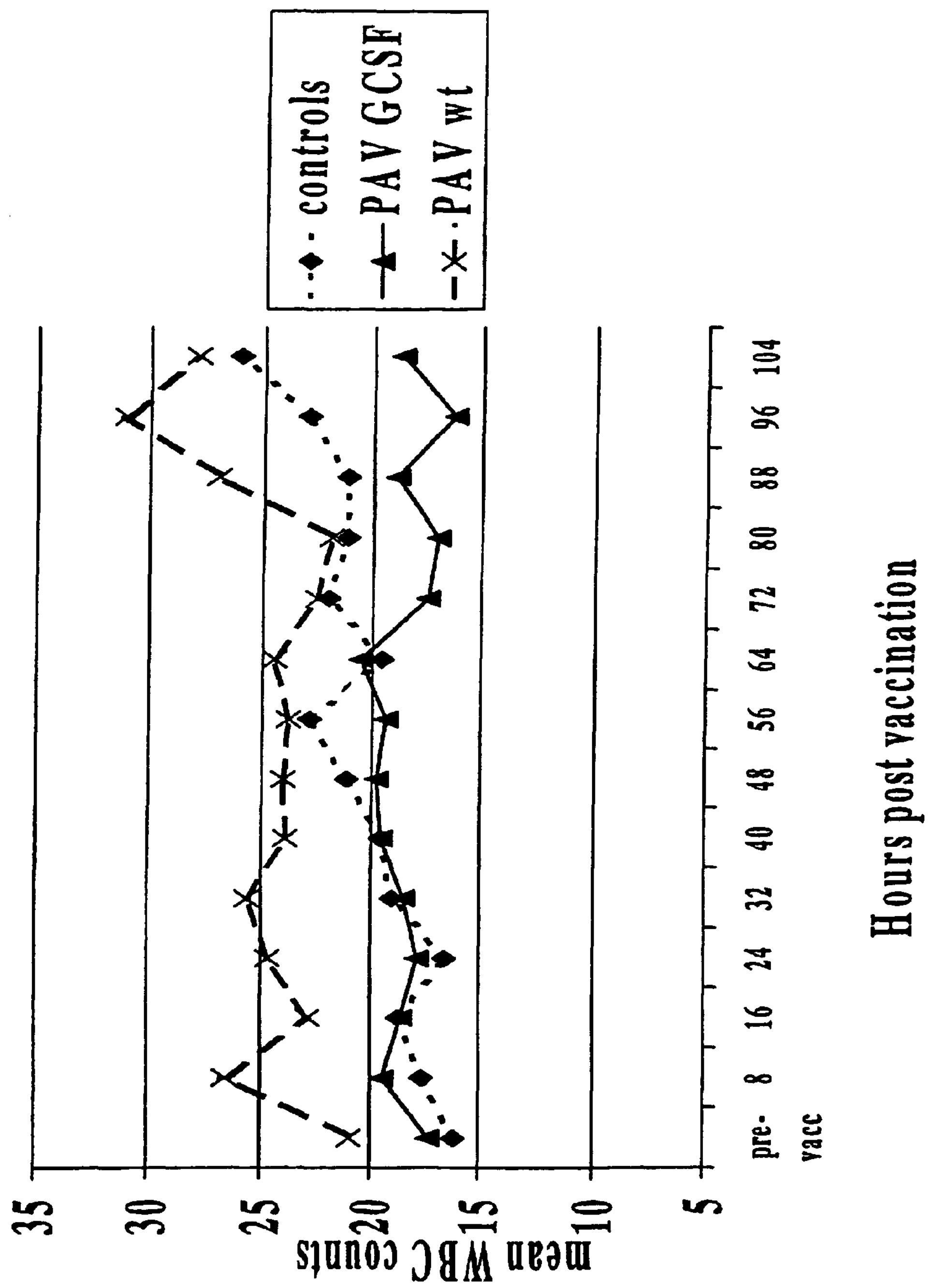
FIG. 10 graphically illustrates the mean white blood cell (WBC) counts of pigs vaccinated with a recombinant PAV vaccine expressing porcine G-CSF.
Figure 11:
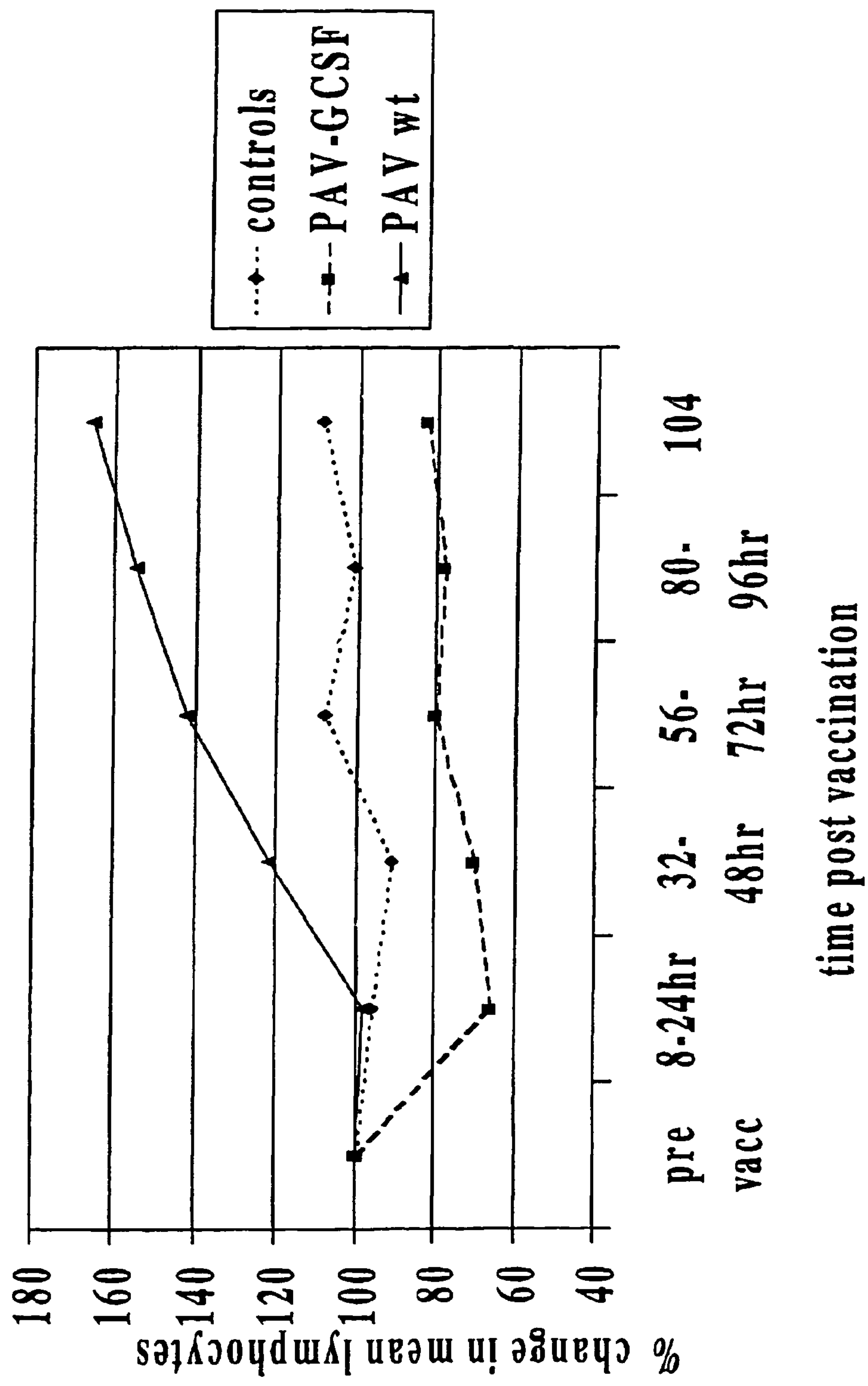
FIG. 11 graphically illustrates the percentage change in white blood cell (WBC) counts following vaccination with a recombinant PAV vaccine expressing porcine G-CSF.

In this experiment 5-6 week old piglets were used to represent immunocompetent pigs. A group of pigs (n=4) were vaccinated with recombinant PAV-G-CSF administered subcutaneously at a dose of $1\times10^7$ pfu per piglet A second group (n=4) were vaccinated with PAV wild type (wt) administered subcutaneously at a dose of $1\times10^7$ pfu per piglet A control group (n=4) were unvaccinated. Pigs were bled at 8 hour intervals for a period of 104 hours post vaccination. Complete blood counts were determined and the mean white blood cell (WBC) counts for each group monitored. These results are graphically represented in FIG. 10 and the percentage change in mean WBC counts graphically represented in FIG. 11.

Pigs vaccinated with either PAV wt or PAV-G-CSF showed clinical signs of disease with mild diahorrea 24-72 hours post vaccination. Both groups of pigs were completely recovered by 80-96 hours post-vaccination. Control pigs showed no clinical signs of disease.

Complete blood screening results show that the mean WBC counts for control pigs increased over the duration of the experiment.

PAV wt vaccinated pigs also show an increase in WBC counts, with a depression in WBC counts between 48-80 hours post-vaccination and recovery from 80-96 hours onwards.

Pigs vaccinated with the recombinant PAV-G-CSF show a significant depression in WBC counts over the duration of the experiment A statistical analysis of these results is tabulated in Table 3. The analysis shows that differences between the mean WBC counts (controls and PAV-G-CSF; PAV wt and PAV-G-CSF) were significant indicating that the recombinant PAV-G-CSF altered the proportions of cells involved with immunity.

TABLE 3

Results of t-tests between mean WBC counts of groups of pigs vaccinated with either PAV wild type (wt), PAV recombinant expressing G-CSF (PAV-G-CSF) or unvaccinated controls.

| | Pre vacc 0 hr | 8-24 hr[d] | 32-48 hr | 56-72 hr | 80-104 hr |
|---|---|---|---|---|---|
| Control vs PAV-G-CSF[a] | $p > 0.2$[b] | $P > 0.2$ | $P > 0.2$ | $P > 0.2$ | $P < 0.005$ |
| Control vs PAV wt | $p > 0.1$ | $p > 0.01$[c] | $p > 0.02$ | $p > 0.2$ | $P < 0.05$ |
| PAV-G-CSF Vs PAV wt | $p > 0.2$ | $p > 0.05$ | $p > 0.05$ | $P < 0.05$ | $P < 0.001$ |

[a]null hypothesis; them is no difference between the mean WBC counts.
[b]$p > 0.05$, insufficient to reject the null hypotheses at the 95% confidence level, conclude that there is no difference between mean leucocyte levels.
[c]$p < 0.05$, null hypothesis rejected at 95% confidence level, conclude that there is a difference between the mean leucocyte levels.
[d]4 pigs in each group were bled at 8 hour intervals.

Figure 12:
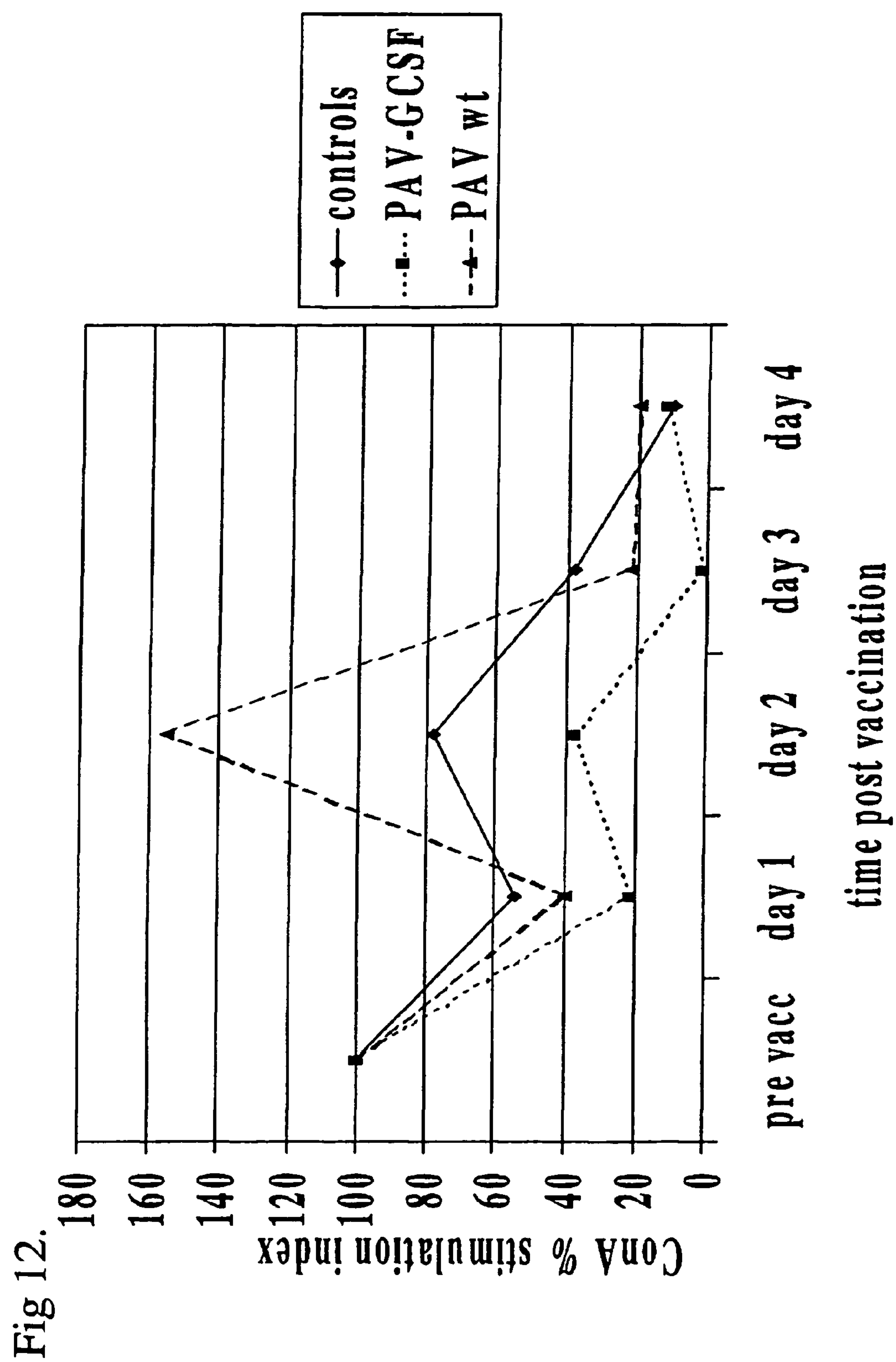
FIG. 12 graphically represents the percentage change in monocyte cell populations following vaccination with recombinant PAV-G-CSF.
Figure 13:
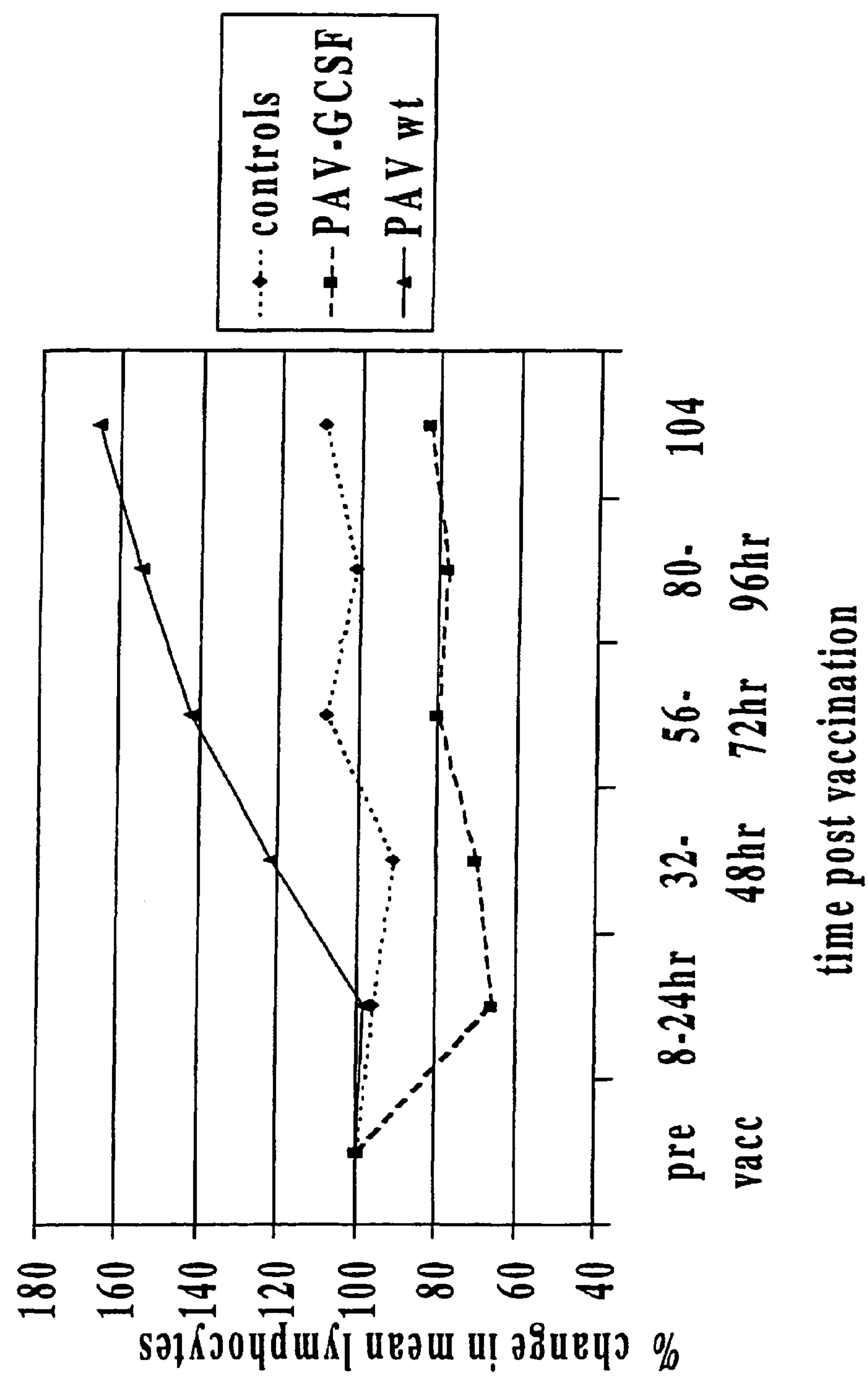
FIG. 13 graphically represents the percentage change in lymphocyte cell populations following vaccination with recombinant PAV-G-CSF.

Differential WBC counts were also determined and monitored for each group. The percentage change in mean monocyte cell populations graphically represented in FIG. 12 and the percentage change in mean lymphocyte cell populations graphically represented in FIG. 13. FIG. 12 shows that monocyte cell populations increased rapidly in pigs following vaccination with PAV wt, but were suppressed by vaccination with the recombinant PAV-G-CSF. This effect was due to the expression of G-CSF by the recombinant. A statistical analysis of these results is tabulated in Table 4. The analysis shows that there was a significant difference between the PAV wt and PAV-G-CSF from 32 to 96 hours post vaccination. FIG. 13 shows that there were shifts in lymphocyte cell population numbers following vaccination with the recombinant PAV-G-CSF. Unvaccinated controls show stable lymphocyte cell numbers over the duration of the experiment, whereas pigs vaccinated with PAV wt show a significant increase in lymphocyte cell population as a response to infection. Pigs vaccinated with the recombinant PAV-G-CSF show a decline in lymphocyte cell population. A statistical analysis of these results is tabulated in Table 5. The analysis shows that there was a significant difference between PAV wt and the recombinant PAV-G-CSF between 8 and 96 hours post vaccination. The different responses in lymphocyte cell proliferation following vaccination with recombinant PAV-G-CSF and PAV wt were due to the expression of G-CSF by the recombinant These results show that vaccination with recombinant PAV-G-CSF produces a shift in sub-populations of cells involved in immunity.

TABLE 4

Results of t-tests between mean monocyte cell populations following vaccination of pigs with either recombinant PAV-G-CSF, wild type PAV (PAV wt) or unvaccinated controls.

| | Pre vacc | 8-24 hr[d] | 32-48 hr | 56-72 hr | 80-96 hr | 104 hr |
|---|---|---|---|---|---|---|
| Control Vs PAV-G-CSF[a] | p > 0.1[b] | P > 0.2 | P > 0.2 | P > 0.2 | P > 0.2 | p > 0.2 |
| Control Vs PAV wt | p > 0.2 | P < 0.002[c] | p > 0.2 | P < 0.001[c] | P > 0.2 | p > 0.2 |
| PAV wt Vs PAV-G-CSF | p > 0.2 | P < 0.001 | p > 0.2 | P > 0.2 | P > 0.2 | p > 0.05 |

[a]null hypothesis; there is no difference between the mean monocyte cell counts.
[b]p > 0.1, insufficient to reject the null hypothesis at the 90% confidence level, conclude that there is no difference between mean monocyte cell levels.
[c]p < 0.05, null hypothesis rejected at 95% confidence level, conclude that there is a difference between the mean monocyte cell levels
[d]4 pigs in each group were bled at 8 hour intervals

TABLE 5

Results of t-tests between mean lymphocyte cell populations following vaccination of pigs with either recombinant PAV-G-CSF, wild type PAV (PAV wt) or unvaccinated controls.

| | Pre vacc | 8-24 hr[d] | 32-48 hr | 56-72 hr | 80-96 hr | 104 hr |
|---|---|---|---|---|---|---|
| Control Vs PAV-G-CSF[a] | p > 0.2 | P > 0.05[b] | P > 0.2 | P > 0.2 | P > 0.2 | p > 0.2 |
| Control Vs PAV wt | p > 0.2 | P > 0.2 | P < 0.01[c] | P < 0.001[c] | P < 0.001[c] | p > 0.2 |
| PAV wt Vs PAV-G-CSF | p > 0.2 | P < 0.05[c] | P < 0.002[c] | P < 0.005[c] | P < 0.001[c] | p > 0.05 |

Figure 14:
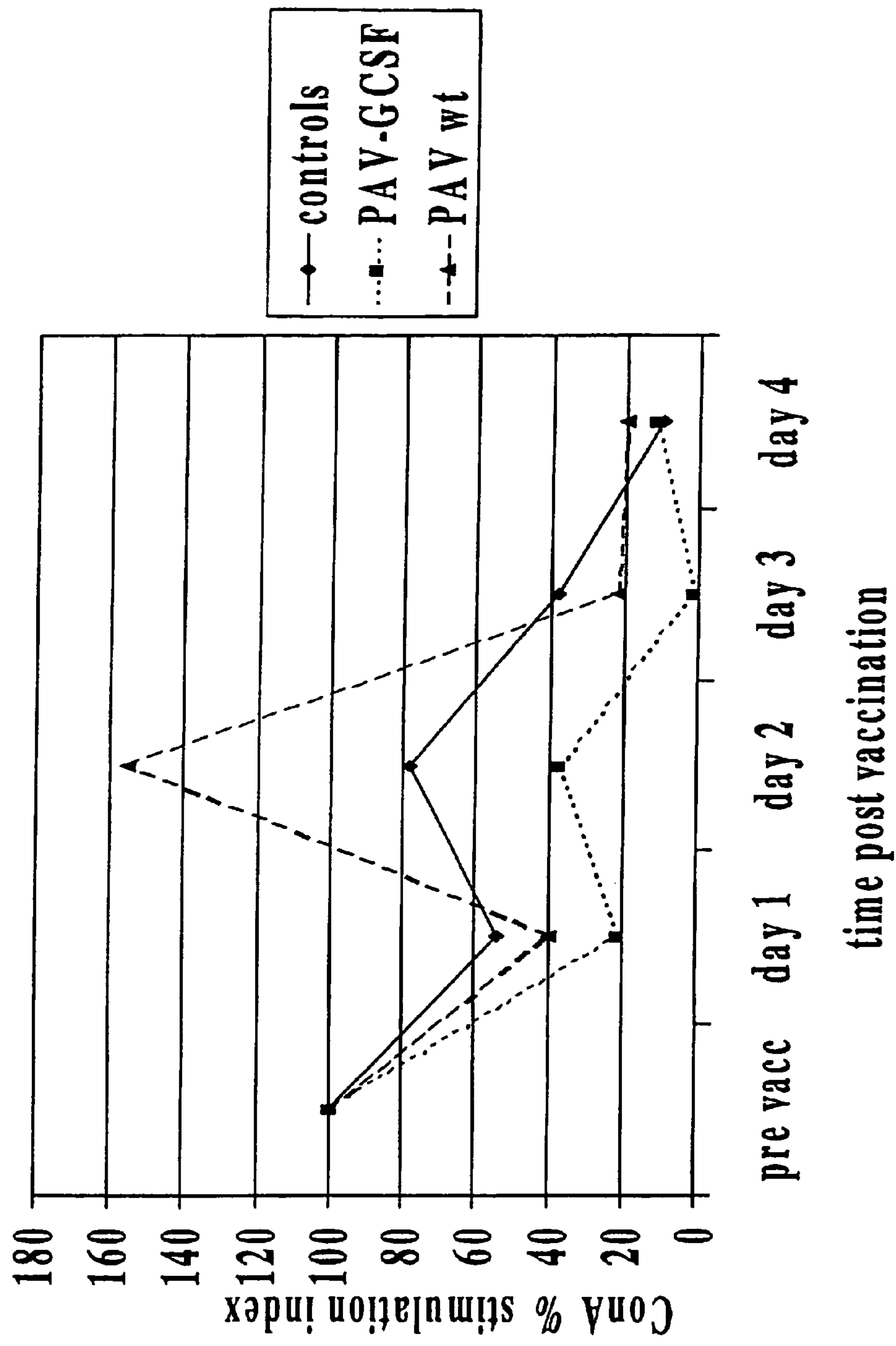
FIG. 14 graphically represents the change in stimulation of T-cells following vaccination with recombinant PAV-G-CSF.

[a]null hypothesis; there is no difference between the mean lymphocyte cell counts.
[b]p > 0.05, insufficient to reject the null hypothesis at the 95% confidence level, conclude that there is no difference between mean lymphocyte cell levels.
[c]p < 0.05, null hypothesis rejected at 95% confidence level, conclude that there is a difference between the mean lymphocyte cell levels.
[d]4 pigs in each group were bled at 8 hour intervals FIG. 14 graphically represents changes in the proliferation of T cells of each group following stimulation with Concanavalin A (Con A). These results confirm that there was a significant proliferation of T-cells following vaccination with PAV wt at day 2 post vaccination, whereas vaccination with the recombinant PAV-G-CSF resulted in a suppression of T-cell proliferation by day 3.

The results of vaccination with a recombinant PAV expressing porcine G-CSF shows that G-CSF has a significant effect on the cells involved with immune responses.

It will be appreciated that whilst this document establishes the metes and bounds of this invention, all embodiments falling within its scope for example with regard to heterologous genes, insertion sites, types of promoter and senotype have not necessarily been specifically exemplified although it is intended that they should fall within the scope of protection afforded this invention.

FIG. 2

Total sequence of the PAV Major Late Promoter cassette (SEQ ID NO:1) including the added nucleotides 5' (upstream) of the USF.

Nucleotide base count: 76 A 143 C 187 G 96 T Total 502 bp

1 GGTGCCGCGG TCGTCGGCGT AGAGGATGAG GGCCCAGTCG GAGATGAAGG CACGCGCCCA

61 GGCGAGGACG AAGCTGGCGA CCTGCGAGGG GTAGCGGTCG TTGGGCACTA ATGGCGAGGC

121 CTGCTCGAGC GTGTGGAGAC AGAGGTCCTC GTCGTCCGCG TCCAGGAAGT GGATTGGTCG

181 CCAGTGGTAG TCCACGTGAC CGGCTTGCGG GTCGGGGGGT ATAAAAGGCG CGGGCCGGGG

241 TGCGTGGCCG TCA*GTTGCTT CGCAGGCCTC GTCACCGGAG TCCGCGTCTC CGGCGTCTCG*

-continued

```
301 CGCTGCGGCT GCATCTGTGG TCCCGGAGTC TTCAGGTCCT TGTTGAGGAG GTACTCCTGA

361 TCGCTGTCCC AGTACTTGGC GTGTGGGAAG CCGTCCTGAT CGCGATCCTC CTGCTGTTGC

421 AGCGCTTCGG CAAACACGCG CACCTGCTCT TCGGACCCGG CGAAGCGTTC GACGAAGGCG

481 TCTAGCCAGC AACAGTCGCA AG
```

Total sequence of the PAV Major Late Promoter cassette (SEQ ID NO:1) including the added nucleotides 5' (upstream) of the USF. The Upstream Stimulatory Factor (USF) and TATA motiff are in bold. The complete leader sequence is italised with the cap site and splice sites between the individual leaders indicated by double underlining or single underlining respectively.

FIG. 3 Individual sequences of the Promoter cassette components. The 5' (upstream) sequence included in the long cassette=SEQ ID NO:2; the sequence including the USF, TATA motif and sequence to the cap site=SEQ ID NO:3; the first leader sequence=SEQ ID NO:4; the second leader sequence=SEQ ID NO:5; the third leader sequence=SEQ ID NO:6.

Individual sequences of the Promoter cassette components:

I. The 5' (upstream) sequence included in the long cassette.

```
  1 GGTGCCGCGG TCGTCGGCGT AGAGGATGAG GGCCCAGTCG GAGATGAAGG CACGCGCCCA

 61 GGCGAGGACG AAGCTGGCGA CCTGCGAGGG GTAGCGGTCG TTGGGCACTA ATGGCGAGGC

121 CTGCTCGAGC GTGTGGAGAC AGAGGTCCTC GTCGTCCGCG TCCAGGAAGT GGATTGGTCG

181 CCAGTGGTAG
```

II. Sequence including the USF, TATA motiff and sequence to the cap site.

```
 1 CCACGTGACC GGCTTGCGGG TCGGGGGGTA TAAAAGGCGC GGGCCGGGGT GCGTGGCCGT

61 C
```

III. First leader sequence.

```
 1 AGTTGCTTCG CAGGCCTCGT CACCGGAGTC CGCGTCTCCG GCGTCTCGCG CTGCGGCTGC

61 ATCTGTGGTC CCGGAGTCTT CAG
```

IV. Second leader sequence.

```
 1 GTCCTTGTTG AGGAGGTACT CCTGATCGCT GTCCCAGTAC TTGGCGTGTG GGAAGCCGTC

61 CTGATCG
```

V. Third leader sequence.

```
 1 CGATCCTCCT GCTGTTGCAG CGCTTCGGCA AACACGCGCA CCTGCTCTTC GGACCCGGCG

61 AAGCGTTCGA CGAAGGCGTC TAGCCAGCAA CAGTCGCAAG
```

FIG. 4

FIG. 4 Sequence of the right hand end of the PAV genome this area being a proposed site for insertion of expression cassettes (SEQ ID NO:7).

Sequence of the right hand end of the PAV genome this area being a proposed site for insertion of expression cassettes.

Nucleotide base count 183 A 255 C 306 G 204 T Total 948 bases

1 CATCATCAAT AATATACCGC ACACTTTTAT TGCCCCTTTT GTGGCGTGGT GATTGGCGGA

61 GAGGGTTGGG GGCGGCGGGC GGTGATTGGT GGAGAGGGGT GTGACGTAGC GTGGGAACGT

121 GACGTCGCGT GGGAAAATAA CGTGGCGTGG GAACGGTCAA AGTCCGAGGG GCGGGGTCAA

181 AGTCCGCAGT CGCGGGGCGG AGCCGGCTGG CGGGAATTCC CGGGACTTTC TGGGCGGGTA
EcoRI SmaI

241 ATCGTTAACG CGGAGGCGGG GGAATTCCGA TCGGACGATG TGGTACTGAT TAACCGACCG
HpaI EcoRI

301 CAGGCGTGTC CACATCCGCT GTGGGTATAT CACCGGCGCT CGCGGTGTTC GCTCACACTC

361 GTCTCGGCGC TGTCACAGAG AGAGACACTG AGAGCGAGAC GAGGAGAAAC CGAAAGCGGG

421 GCAGGAGGAG TCACCGGGCC ATCTTCCCAT CAGAGCCCTC TCATGGCCCA CGACCGACTG

481 CTGCTGGCCG CGGTGGCTGA CTGTTGCTCG CCGTGCTCTA TCTGTACTTC GCCTACCTCG

541 CGTGGCAGGA TCGGGACACT CTTCACACTC AGGAGGCCGC CTCTCCTCGC TTCTTCATCG

601 GGTCCAACCA CCAGCCCTGG TGCCCGGATT TTGATTGGCA GGAGCAGGAC GAGCACACTC

661 ACTAGACGTT TAGAAAAAAG ACACACATTG GAACTCATAT ATGTCTGCGG GACCGCATCA

721 GCAGCCCGGT CTGCTGTTGG CTGCGGGTGA GAGGCCTCCG GTAATTCATC AGAACCGCAT
StuI

781 TCATCTGCGC CACGTCCCGA CATATGGTGC TGACGTCAGA ACAGCCCAGC GTGATCCTTT
SacIII

841 TAATGTGCTA GTCTACGTGC CCACTGGGTT TGCTGTGTTT GTGCCGACTG AGCGAGATTT

901 TCAGAGGAGG GATCTGGTCC GTTTCCAGAC CTGCTGCTTC CGGCATCA

The Inverted Terminal Repeat (ITR) is shown in bold. Enzyme sites of interest are underlined with the enzyme name below. Putative TATA for E4 region is also shown.

---

The invention claimed is:

1. A method of vaccination of pigs against disease comprising administering to said pigs a first recombinant porcine adenovirus (PAV) vector stably incorporating, and expressing a heterologous nucleotide sequence encoding at least one antigenic determinant of said disease against which vaccination is desired, wherein said heterologous nucleotide sequence is inserted into a non-essential region of a site selected from the group consisting of the E3 region and map units 97-99.5 of PAV-3 wherein said PAV3 vector further comprises a heterologous nucleotide sequence encoding PAV-4 fiber.

2. A method as claimed in claim 1 including administering to said pig a second porcine adenovirus vector including at least one heterologous nucleotide sequence which differs from a heterologous nucleotide sequence incorporated in said first recombinant porcine adenovirus vector.

3. A method as claimed claim 1 wherein said second porcine adenovirus vector incorporates and expressing of at least one heterologous nucleotide sequence encoding an immunopotentiating molecule.

4. The method of claim 1 wherein said recombinant PAV-3 vector comprises said heterologous nucleotide sequence encoding at least one antigenic determinant of said disease against which vaccination is desired and further comprises a heterologous nucleotide sequence that encodes an immunomodulatory molecule.

5. The method of claim 1 wherein the endogenous fiber gene of said PAV 3 has been deleted and the heterologous nucleotide sequence encoding PAV 4 fiber replaces said endogenous fiber gene of PAV-3.

6. The method of claim 1 wherein said PAV-3 comprises the endogenous fiber gene of said PAV 3 and further comprises a nucleotide sequence encoding PAV 4 fiber.

7. A method of vaccination of pigs against disease comprising administering to said pigs a first recombinant porcine adenovirus 3 vector stably incorporating, and expressing a heterologous nucleotide sequence encoding at least one antigenic determinant of said disease against which vaccination is desired, wherein said heterologous nucleotide sequence is inserted into a non-essential region of a site selected from the group consisting of the E3 region and map units 97-99.5 of PAV-3 and a second recombinant porcine adenovirus vector incorporating and expressing a heterologous nucleotide sequence encoding at least one antigenic determinant of said disease against which vaccination is desired.

8. The method of claim 7 wherein said second recombinant adenovirus vector is a PAV-3 recombinant adenovirus vector.

9. The method of claim 7 wherein said second recombinant adenovirus vector is a PAV-4 recombinant adenovirus vector.

10. The method of claim 7 wherein said first and said second recombinant adenovirus vectors are administered simultaneously in a single composition.

11. The method of claim 7 wherein said first and said second recombinant adenovirus vectors are administered sequentially in separate compositions.

12. The method of claim 1 wherein said pigs are vaccinated prior to full immunocompetency.

13. The method of claim 1 wherein said pigs are vaccinated for protection against re-infection subsequent to the initial vaccination.

14. The method of claim 1 wherein said administration is via oral or intranasal delivery.

15. The method of claim 1 wherein said recombinant porcine adenovirus vector is administered in an aerosol formulation.

16. The method of claim 1 wherein said antigenic determinant is an antigenic determinant of infectious agents causing an intestinal disease in pigs.

17. The method of claim 1 wherein said antigenic determinant is an antigenic determinant of infectious agents causing a respiratory disease in pigs.

18. The method of claim 1 wherein said heterologous nucleotide sequence encodes an antigenic determinant selected from the group consisting of an antigenic determinant of pseudorabies virus (Aujeszky's disease virus); an antigenic determinant of glycoprotein D of pseudorabies virus; antigenic determinant of porcine respiratory and reproductive syndrome virus (PRRSV); an antigenic determinant of Hog cholera virus; an antigenic determinant of Swine dysentery, an antigenic determinant of African Swine fever; an antigenic determinant of Japanese encephalitis; an antigenic determinant of porcine parvovirus; an antigenic determinant of porcine cornavirus; an antigenic determinant of porcine rotavirus; an antigenic determinant of porcine parainfluenza virus; and an antigenic determinant of Mycoplasma hyopneumonia.

19. The method of claim 1 wherein said recombinant porcine adenovirus further comprises a heterologous nucleotide sequence selected from a group consisting of a sequence that encodes FMS-like tyrosine kinase (FLT-3) ligand; a heterologous nucleotide sequence that encodes interleukin-3 (IL-3); a heterologous nucleotide sequence that encodes interleukin 4 (IL-4); a heterologous nucleotide sequence that encodes gamma interferon; a heterologous nucleotide sequence that encodes porcine granulocyte macrophage colony stimulating factor (GM-CSF); and a heterologous nucleotide sequence that encodes granulocyte colony stimulating factor (G-CSF).

20. A vaccine composition comprising a first recombinant porcine adenovirus vector that comprises and is capable of expressing a stably incorporated heterologous nucleotide sequence encoding at least one antigenic determinant of a pig disease against which vaccination is desired, wherein said heterologous nucleotide sequence is inserted into a non-essential region of a site selected from the group consisting of the E3 region and map units 97-99.5 of PAV-3 wherein said PAV-3 vector further comprises a heterologous nucleotide sequence encoding PAV-4 fiber.

21. The vaccine composition of claim 20 further comprising a recombinant porcine adenovirus type 4 (PAV-4) vector that comprises and is capable of expressing a stably incorporated heterologous nucleotide sequence encoding at least one antigenic determinant of a pig disease against which vaccination is desired.

22. A vaccine composition comprising a first recombinant porcine adenovirus vector that comprises and is capable of expressing a stably incorporated heterologous nucleotide sequence encoding at least one antigenic determinant of a pig disease against which vaccination is desired, wherein said heterologous nucleotide sequence is inserted into a non-essential region of a site selected from the group consisting of the E3 region and map units 97-99.5 of PAV-3 wherein said PAV-3 vector further comprises a heterologous nucleotide sequence encoding PAV-4 fiber, said vaccine composition further comprising a recombinant porcine adenovirus type 4 (PAV-4) vector that comprises and is capable of expressing a stably incorporated heterologous nucleotide sequence encoding at least one antigenic determinant of a pig disease against which vaccination is desired wherein said recombinant PAV-3 vector and said recombinant PAV-4 vector are both in one pharmaceutical composition.

23. A vaccine composition comprising of two separate pharmaceutical formulation, wherein the first formulation comprises a first recombinant porcine adenovirus vector that comprises and is capable of expressing a stably incorporated heterologous nucleotide sequence encoding at least one antigenic determinant of a pig disease against which vaccination is desired, wherein said heterologous nucleotide sequence is inserted into a non-essential region of a site selected from the group consisting of the E3 region and map units 97-99.5 of PAV-3 wherein said PAV-3 vector further comprises a heterologous nucleotide sequence encoding PAV-4 fiber, and the second pharmaceutical formulation comprises a recombinant porcine adenovirus type 4 (PAV-4) vector that comprises and is capable of expressing a stably incorporated heterologous nucleotide sequence encoding at least one antigenic determinant of a pig disease against which vaccination is desired.

24. The vaccine composition of claim 20 wherein said heterologous nucleotide encodes antigenic determinants of infectious agents that cause intestinal diseases in pigs.

25. The vaccine composition of claim 20 wherein said heterologous nucleotide sequence encodes antigenic determinants of infectious agents causing respiratory diseases in pigs.

26. The vaccine composition of claim 20 wherein said heterologous nucleotide sequence encodes an antigenic determinant of pseudorabies virus (Aujeszky's disease virus).

27. The vaccine composition of claim 20 wherein said heterologous nucleotide sequence encodes an antigenic determinant of glycoprotein D of pseudorabies virus.

28. The vaccine composition of claim 20 wherein said heterologous nucleotide sequence encodes an antigenic determinant of porcine respiratory and reproductive syndrome virus (PRRSV).

29. The vaccine composition of claim 20 wherein said heterologous nucleotide sequence encodes an antigenic determinant of Hog cholera virus.

30. The vaccine composition of claim 20 wherein said heterologous nucleotide sequence encodes an antigenic determinant of porcine parvovirus.

31. The vaccine composition of claim 20 wherein said heterologous nucleotide sequence encodes an antigenic determinant of porcine cornavirus.

32. The vaccine composition of claim 20 wherein said heterologous nucleotide sequence encodes an antigenic determinant of porcine rotavirus.

33. The vaccine composition of claim 20 wherein said heterologous nucleotide sequence encodes an antigenic determinant of porcine parainfluenza virus.

34. The vaccine composition of claim 20 wherein said heterologous nucleotide sequence encodes an antigenic determinant of Mycoplasma hyopneumonia.

35. The vaccine composition of claim 20 wherein said recombinant porcine adenovirus further comprises a heterologous nucleotide sequence that encodes FMS-like tyrosine kinase (FLT-3) ligand.

36. The vaccine composition of claim 20 wherein said recombinant porcine adenovirus further comprises a heterologous nucleotide sequence that encodes interleukin-3 (IL-3).

37. The vaccine composition of claim 20 wherein said recombinant porcine adenovirus further comprises a heterologous nucleotide sequence that encodes interleukin 4 (IL-4).

38. The vaccine composition of claim 20 wherein said recombinant porcine adenovirus further comprises a heterologous nucleotide sequence that encodes gamma interferon.

39. The vaccine composition of claim 20 wherein said recombinant porcine adenovirus further comprises a heterologous nucleotide sequence that encodes porcine granulocyte macrophage colony stimulating factor (GM-CSF).

40. The vaccine composition of claim 20 wherein said recombinant porcine adenovirus further comprises a heterologous nucleotide sequence that encodes granulocyte colony stimulating factor (G-CSF).

41. A method of vaccination of pigs to optimize protection against disease comprising administering to said pigs a first recombinant porcine adenovirus 3 vector stably incorporating, and expressing a heterologous nucleotide sequence encoding at least one immuno-potentiator, wherein said heterologous nucleotide sequence is inserted into a non-essential region of a site selected from the group consisting of the E3 region and map units 97-99.5 of PAV-3.

42. The method of claim 41, wherein said immunopotentiator is a cytokine or a growth promoter.

43. The method of claim 41 wherein said immunopotentiator is selected from the group consisting of a sequence that encodes FMS-like tyrosine kinase (FLT-3) ligand; a heterologous nucleotide sequence that encodes interleukin-3 (IL-3); a heterologous nucleotide sequence that encodes interleukin 4 (IL-4); a heterologous nucleotide sequence that encodes gamma interferon; a heterologous nucleotide sequence that encodes porcine granulocyte macrophage colony stimulating factor (GM-CSF); and a heterologous nucleotide sequence that encodes granulocyte colony stimulating factor (G-CSF).

44. The method of claim 7 wherein said pigs are vaccinated with either said first or said second vector, or both said first and said second vector prior to full immunocompetency.

45. The method of claim 7 wherein said pigs are vaccinated either said first or said second vector, or both said first and said second vector for protection against re-infection subsequent to the initial vaccination.

46. The method of claim 7 wherein said administration of either said first or said second vector, or both said first and said second vector, is via oral or intranasal delivery.

47. The method of claim 7 wherein said said first recombinant porcine adenovirus vector, or said second recombinant adenovirus vector or both said first and said second recombinant adenovirus vector is administered in an aerosol formulation.

48. The method of claim 7 wherein said antigenic determinant in said first recombinant adenovirus vector is an antigenic determinant of infectious agents causing an intestinal disease in pigs.

49. The method of claim 7 wherein said antigenic determinant in said second recombinant adenovirus vector is an antigenic determinant of infectious agents causing an intestinal disease in pigs.

50. The method of claim 7 wherein said antigenic determinant in both said first and said second recombinant adenovirus vectors is an antigenic determinant of infectious agents causing an intestinal disease in pigs.

51. The method of claim 7 wherein said antigenic determinant in said first recombinant adenovirus vector is an antigenic determinant of infectious agents causing a respiratory disease in pigs.

52. The method of claim 7 wherein said antigenic determinant in said second recombinant adenovirus vector is an antigenic determinant of infectious agents causing a respiratory disease in pigs.

53. The method of claim 7 wherein said antigenic determinant in both said first and said second recombinant adenovirus vectors is an antigenic determinant of infectious agents causing a respiratory disease in pigs.

54. The method of claim 7 wherein said heterologous nucleotide sequence in said first recombinant adenovirus vector encodes an antigenic determinant selected from the group consisting of an antigenic determinant of pseudorabies virus (Aujeszky's disease virus); an antigenic determinant of glycoprotein D of pseudorabies virus; antigenic determinant of porcine respiratory and reproductive syndrome virus (PRRSV); an antigenic determinant of Hog cholera virus; an antigenic determinant of Swine dysentery, an antigenic determinant of African Swine fever; an antigenic determinant of Japanese encephalitis; an antigenic determinant of porcine parvovirus; an antigenic determinant of porcine cornavirus; an antigenic determinant of porcine rotavirus; an antigenic determinant of porcine parainfluenza virus; and an antigenic determinant of Mycoplasma hyopneumonia.

55. The method of claim 7 wherein said heterologous nucleotide sequence in said second recombinant adenovirus vector encodes an antigenic determinant selected from the group consisting of an antigenic determinant of pseudorabies virus (Aujeszky's disease virus); an antigenic determinant of glycoprotein D of pseudorabies virus; antigenic determinant of porcine respiratory and reproductive syndrome virus (PRRSV); an antigenic determinant of Hog cholera virus; an antigenic determinant of Swine dysentery, an antigenic determinant of African Swine fever; an antigenic determinant of Japanese encephalitis; an antigenic determinant of porcine parvovirus; an antigenic determinant of porcine cornavirus; an antigenic determinant of porcine rotavirus; an antigenic determinant of porcine parainfluenza virus; and an antigenic determinant of Mycoplasma hyopneumonia.

56. The method of claim 7 wherein said heterologous nucleotide sequence in said first recombinant adenovirus vector encodes a different antigenic determinant from the antigenic determinant encoded in said second recombinant vector.

57. The method of claim 7 wherein said first recombinant porcine adenovirus further comprises a heterologous nucleotide sequence selected from a group consisting of a sequence that encodes FMS-like tyrosine kinase (FLT-3) ligand; a heterologous nucleotide sequence that encodes interleukin-3 (IL-3); a heterologous nucleotide sequence that encodes interleukin 4 (IL-4); a heterologous nucleotide sequence that encodes gamma interferon; a heterologous nucleotide sequence that encodes porcine granulocyte macrophage colony stimulating factor (GM-CSF); and a heterologous nucleotide sequence that encodes granulocyte colony stimulating factor (G-CSF).

58. The method of claim 7 wherein said second recombinant porcine adenovirus further comprises a heterologous nucleotide sequence selected from a group consisting of a sequence that encodes FMS-like tyrosine kinase (FLT-3)

ligand; a heterologous nucleotide sequence that encodes interleukin-3 (IL-3); a heterologous nucleotide sequence that encodes interleukin 4 (IL-4); a heterologous nucleotide sequence that encodes gamma interferon; a heterologous nucleotide sequence that encodes porcine granulocyte macrophage colony stimulating factor (GM-CSF); and a heterologous nucleotide sequence that encodes granulocyte colony stimulating factor (G-CSF).

* * * * *